United States Patent
Fernandez Casares et al.

(10) Patent No.: US 11,117,868 B2
(45) Date of Patent: Sep. 14, 2021

(54) EDARAVONE SALT

(71) Applicant: Treeway TW001 B.V., Rotterdam (NL)

(72) Inventors: Ana Fernandez Casares, Rotterdam (NL); Ronald Van Der Geest, Rotterdam (NL); Sytske Hyke Moolenaar, Rotterdam (NL)

(73) Assignee: TREEWAY TW001 B.V., Rotterdam (NL)

( * ) Notice: Subject to any disclaimer, the term of this patent is extended or adjusted under 35 U.S.C. 154(b) by 0 days.

(21) Appl. No.: 16/846,021

(22) Filed: Apr. 10, 2020

(65) Prior Publication Data
US 2020/0308120 A1    Oct. 1, 2020

Related U.S. Application Data

(63) Continuation of application No. PCT/EP2018/077918, filed on Oct. 12, 2018.

(30) Foreign Application Priority Data

Oct. 13, 2017 (EP) .................... 17196400

(51) Int. Cl.
*C07D 231/22* (2006.01)

(52) U.S. Cl.
CPC ........ *C07D 231/22* (2013.01); *C07B 2200/13* (2013.01)

(58) Field of Classification Search
CPC .................................................. C07D 231/22
See application file for complete search history.

(56) References Cited

U.S. PATENT DOCUMENTS

| 3,764,321 A | 10/1973 | Konig et al. |
| 2008/0070973 A1 | 3/2008 | Anderton et al. |
| 2010/0093816 A1 | 4/2010 | Avitabile et al. |
| 2011/0195943 A9 | 8/2011 | Puig Duran et al. |

FOREIGN PATENT DOCUMENTS

| WO | WO-2008/095720 A1 | 8/2008 |
| WO | WO-2008/096149 A2 | 8/2008 |
| WO | WO-2013/139712 | 9/2013 |

OTHER PUBLICATIONS

Amyotrophic lateral sclerosis [online] retrieved from the internet on Mar. 27, 2021; URL: https://www.cdc.gov/dotw/als/index.html.*
Amyotrophic lateral sclerosis [online] retrieved from the internet on Mar. 27, 2021; URL: https://www.mayoclinic.org/diseases-conditions/amotrophic-lateral-sclerosis.*
International Search Report received in corresponding International Application No. PCT/EP2018/077918, 4 pages.
Veverka et al.: "Edaravone cocrystals: synthesis, screening, and preliminary characterization", Monatshefte Fur Chemie—Chemical Monthl vol. 144, No. 9, Sep. 2013 (Sep. 2013) pp. 1335-1349, XP002779568.

* cited by examiner

*Primary Examiner* — Shawquia Jackson
(74) *Attorney, Agent, or Firm* — Foley & Lardner LLP

(57) ABSTRACT

The invention relates to a salt of 3-methyl-1-phenyl-2-pyrazolin-5-one (edaravone), wherein the salt is 3-methyl-1-phenyl-2-pyrazolin-5-one napadisylate or 3-methyl-1-phenyl-2-pyrazolin-5-one hemi-napadisylate. These napadisylate salts of edaravone are easy to manufacture and dissolve more rapidly in water than the free edaravone base. In addition, the edaravone salts of the present invention are very stable and easy to handle.
The invention also relates to a pharmaceutical composition comprising the aforementioned edaravone salt and to a method of preparing such edaravone salt.

15 Claims, 15 Drawing Sheets

EDARAVONE SALT

CROSS-REFERENCE TO RELATED APPLICATIONS

This application is a continuation of International Application No. PCT/EP2018/077918, filed Oct. 12, 2018, which claims the benefit of and priority to European Application No. 17196400.0, filed Oct. 13, 2017, both of which are hereby incorporated by reference herein in their entireties.

TECHNICAL FIELD OF THE INVENTION

The invention relates to salts of 3-methyl-1-phenyl-2-pyrazolin-5-one (edaravone). More particularly, the invention relates to an edaravone salt selected from 3-methyl-1-phenyl-2-pyrazolin-5-one napadisylate and 3-methyl-1-phenyl-2-pyrazolin-5-one hemi-napadisylate.

BACKGROUND OF THE INVENTION

3-Methyl-1-phenyl-2-pyrazolin-5-one (edaravone), sold under the brand names Radicava® and Radicut®, is an intravenous medication used to help with recovery following a stroke and to treat amyotrophic lateral sclerosis (ALS). Radicut® is sold in 20 mL ampoules containing an aqueous solution of 30 mg edaravone.

Edaravone is sparingly soluble in water (1.85 mg/L in demineralized water at 25° C.). In addition, edaravone dissolves very slowly in water.

An estimated 50% of all drug molecules used in medicinal therapy are administered as salts. A drug substance often has certain suboptimal physicochemical or biopharmaceutical properties that can be overcome by pairing a basic or acidic drug molecule with a counter ion to create a salt version of the drug.

Innumerable salt forms are available to pharmaceutical scientists. The following four parameters are often considered important criteria for the selection of a particular form:
  aqueous solubility measured at various pH values, depending upon the intended pharmaceutical profile;
  high degree of crystallinity;
  low hygroscopicity (i.e., water absorption versus relative humidity), which gives consistent performance (e.g. dosage uniformity);
  optimal chemical and solid-state stability under accelerated conditions (i.e., minimal chemical degradation or solid-state changes when stored at 40° C. and 75% relative humidity);
  limited number of polymorphs or absence of variability because of polymorphism;
  ease of synthesis, handling, and formulation development.

Veverka et al. (*Edaravone cocrystals: synthesis, screening, and preliminary characterization*, Monatshefte für Chemie—Chemical Monthly, September 2013, Volume 144, Issue 9, pp 1335-1349) constructed cocrystals of edaravone and phenolic acids. Edaravone cocrystals were prepared at various molar ratios. Representative samples of the cocrystals were exposed to accelerated oxidative and thermal stress to investigate their stability. From the stability screening, protocatechuic acid and gallic acid cocrystals were identified as development candidates because they provide stable cocrystal forms.

Napydisylate salts of drugs are known in the art. Mebhydrolin napadisylate is an antihistamine that is sold in a number of countries under the brand names Bexidal and Diazolin.

US 2008/0070973 describes 2-(methyloxy)-N-[2-methyl-1-phenyl-2-(1-pyrrolidinyl)propyl]-4,6-bis(trifluoromethyl)benzamide napadisylate or a solvate thereof.

US 2010/0093816 describes salt being [2-(4-chloro-benzyloxy)-ethyl]-[2-((R)-cyclohexyl-hydroxy-phenyl-methyl)-oxazol-5-ylmethyl]-dimethyl-ammonium napadisylate.

US 2011/0195943 describes a salt of 5-(2-{[6-(2,2-difluoro-2-phenylethoxy)hexyl]amino}-1-hydroxyethyl)-8-hydroxyquinolin-2(IH)-one; or a pharmaceutically acceptable solvate thereof;
wherein the salt is chosen from crystalline monoapadisylate salt and heminapadisylate salt.

WO 2013/139712 describes a crystalline polymorph of 5-(2-{[6-(2.2-difluoro-2-phenylethoxy)hexyl]amino}-1(R)-hydroxyethyl)-8-hydroxyquinolin-2(171)-one heminapadisylate, which is (i) a hydrate polymorph, or (ii) or a type β polymorph which is obtainable by drying of said hydrate polymorph.

SUMMARY OF THE INVENTION

The inventors have discovered that napadisylate salts of edaravone offer a surprising combination of favourable properties that makes it possible to administer these edaravone salts via non-intravenous routes. The present invention is specifically concerned with the edaravone salts 3-methyl-1-phenyl-2-pyrazolin-5-one napadisylate and 3-methyl-1-phenyl-2-pyrazolin-5-one hemi-napadisylate. The invention also extends to solvates (including hydrates) of these edaravone salts.

The napadisylate salts of edaravone (hereinafter referred to as 'the edaravone salts' or simply 'the salts') are easy to manufacture and dissolve more rapidly in water than the free edaravone base. In addition, the edaravone salts of the present invention are very stable and easy to handle.

DETAILED DESCRIPTION OF THE INVENTION

Figure 1A:
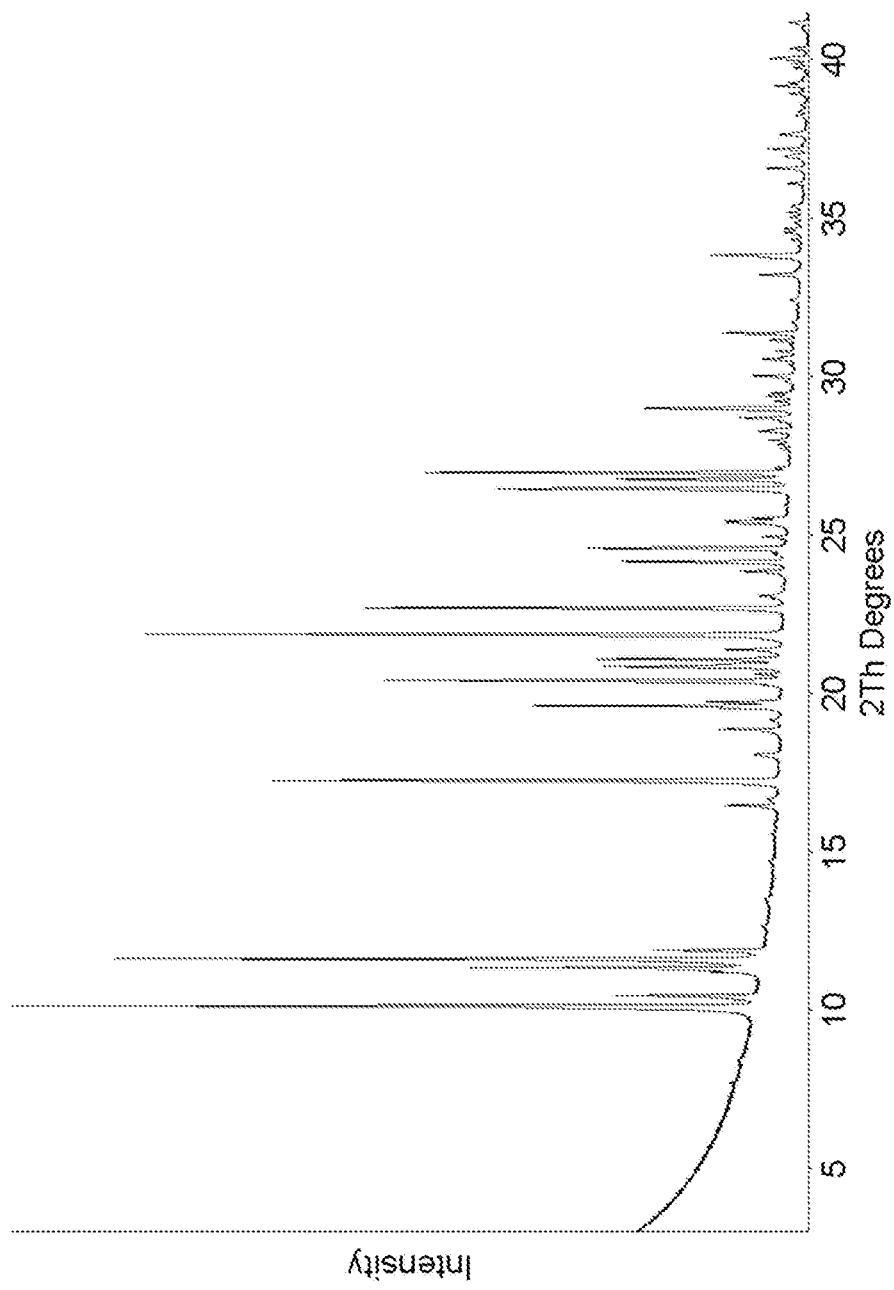
FIG. 1A shows an X-ray powder diffraction pattern of polymorph A.

Accordingly, a first aspect of the invention relates to a salt of 3-methyl-1-phenyl-2-pyrazolin-5-one (edaravone), wherein the salt is 3-methyl-1-phenyl-2-pyrazolin-5-one napadisylate or 3-methyl-1-phenyl-2-pyrazolin-5-one hemi-napadisylate.

The term "salt" as used herein also encompasses solvates of the salt, such as hydrates.

The term "solvate" as used herein refers to a complex of variable stoichiometry formed by the edaravone salt of the present invention and a pharmaceutically acceptable solvent. Examples of suitable solvents include, water, isopropanol, acetonitrile and combinations thereof.

The term "napadisylate" as used herein, unless indicated otherwise, refers to the anionic residue of 1,5-naphthalene-disulfonic acid.

The term "treatment" as used herein, unless indicated otherwise, encompasses therapeutic, palliative and prophylactic treatment.

The term "edaravone equivalent" as used herein refers to the quantity of edaravone (3-methyl-1-phenyl-2-pyrazolin-5-one) that is contained in a given quantity of edaravone salt. The molar mass of edaravone is appr. 174 g/mol. Given that the edaravone salt 3-methyl-1-phenyl-2-pyrazolin-5-one hemi-napadisylate monohydrate has a molar mass of appr. 673 g and that one molecule of this salt contains two edaravone bases, 1000 mg of the latter salt equals 1000×2× 174/673=517 mg edaravone equivalent. In the following table, for a number of edaravone salts the conversion to edaravone equivalents is shown.

|  | Edaravone equivalent of 1000 mg salt (in mg) |
|---|---|
| Edaravone hemi-napadisylate salt (anhydrous) | 547 |
| Edaravone hemi-napadisylate monohydrate salt | 517 |
| Edaravone hemi-napadisylate hemihydrate salt | 532 |
| Edaravone napadisylate salt (anhydrous) | 377 |

According to a particularly preferred embodiment of the present invention the edaravone salt is represented by the following formula:

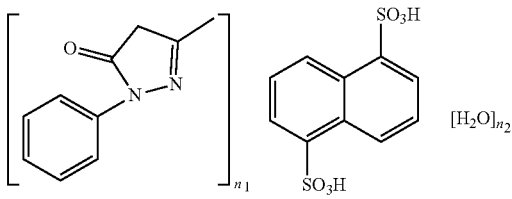

wherein $n_1$ is 1 or 2 and wherein $n_2$ is 0, ½, 1, 2 or 4.

The present invention encompasses both the napadisylate-form ($n_1$=1) and the hemi-napadisylate-form ($n_1$=2) of the edaravone salt. Preferably, the edaravone salt of the present invention is the hemi-napadisylate.

The present invention encompassed both anhydrous and hydrated forms of the edaravone salt. In accordance with one preferred embodiment of the invention, the edaravone salt is anhydrous ($n_2$=0). According to another preferred embodiment, the edaravone salt is the monohydrate salt ($n_1$=1 and $n_2$=1; or $n_1$=2 and $n_2$=2).

Preferably, the edaravone salt is a hemi-napadisylate ($n_1$=2). In case the edaravone salt is a hemi-napadisylate, $n_2$ preferably equals 0, 1 or 2.

According to a particularly preferred embodiment, the edaravone salt of the present invention is edaravone hemi-napadisylate monohydrate ($n_1$=2; $n_2$=2).

The anhydrous from edaravone hemi-napadisylate can easily be transferred into the monohydrate form, e.g. by exposing the anhydrous salt to humid conditions. Thus, the anhydrous hemi-napadisylate salt can suitably be used as an intermediate in the production of the monohydrate.

According to yet another preferred embodiment, the edaravone salt of the present invention is crystalline.

The crystalline structure of the edaravone salt can suitably be determined using X-ray powder diffraction (XRPD). In addition, the melting point and the amount of crystal water can be determined with the help of differential scanning calorimetry (DSC) and Thermo-Gravimetric Analysis (TGA).

The present invention specifically relates to different crystalline forms (polymorphs) of the edaravone salts of the present invention. These polymorphs are described in more detail below.

Edaravone Hemi-Napadisylate Monohydrate Salt—Polymorph A

The polymorph A edaravone salt of the present invention has an X-ray powder diffraction (XRPD) pattern comprising at least 8 peaks, more preferably at least 9 peaks and most preferably at least 10 peaks at diffraction angle 2-theta degrees that are within 0.1 degrees of 10.1, 11.3, 11.6, 17.3, 19.6, 20.4, 20.9, 21.1, 21.9, 22.7, 24.2, 24.6, 26.5 and 27.0 degrees.

According to another preferred embodiment, the XRPD pattern of the polymorph A comprises at least 8 peaks, more preferably at least 9 peaks and most preferably at least 10 peaks at d-spacings that are within 0.05 Angstrom of 8.74, 7.81, 7.62, 5.14, 4.53, 4.35, 4.26, 4.21, 4.06, 3.91, 3.68, 3.62, 3.37 and 3.30 Angstroms.

The following table shows a typical XRPD peak list for the polymorph A of the present invention.

| PEAK | ANGLE (2Θ) | D-SPACING | INTENSITY |
|---|---|---|---|
| 1 | 10.1 | 8.74 | 100 |
| 2 | 11.3 | 7.81 | 44 |
| 3 | 11.6 | 7.62 | 88 |
| 4 | 17.3 | 5.14 | 68 |
| 5 | 19.6 | 4.53 | 36 |
| 6 | 20.4 | 4.35 | 54 |
| 7 | 20.9 | 4.26 | 27 |
| 8 | 21.1 | 4.21 | 28 |
| 9 | 21.9 | 4.06 | 84 |
| 10 | 22.7 | 3.91 | 57 |
| 11 | 24.2 | 3.68 | 25 |
| 12 | 24.6 | 3.62 | 29 |
| 13 | 26.5 | 3.37 | 41 |
| 14 | 27.0 | 3.30 | 49 |

The polymorph A preferably has an X-ray powder diffraction pattern that corresponds to the X-ray powder diffraction pattern shown in FIG. 1a.

The polymorph A of the present invention is preferably characterized by a differential scanning calorimetry (DSC) thermogram with an endothermic peak between 249.5 and 252.8° C. This peak is attributed to the melting of anhydrous edaravone salt. Even more preferred, the DSC thermogram of the edaravone salt shows an additional endothermic peak between 105 and 130° C. The latter endothermic peak is deemed to correspond to the release of crystal water.

DSC is a thermo-analytical technique in which the difference in the amount of heat required to increase the temperature of a sample and a reference is measured as a function of temperature. DSC can be used to measure several characteristic properties of a sample, allowing observation of crystallization events. Specifically, with DSC, it is possible to observe small energy changes that occur as matter transitions from a solid to a liquid crystal and from a liquid crystal to an isotropic liquid. The presence of events in the DSC curve can be used to assess the compound's stability, as well as the presence of solvates.

DSC analyses as described herein were carried out as follows: Approximately 1.5 mg of solid sample was sealed in standard 40 μL aluminum pan, pin-holed and heated in the DSC from 25° C. to 300° C., at a heating rate of 10° C./min. Dry $N_2$ gas, at a flow rate of 50 mL/min was used to purge the DSC equipment during the measurement. Melting properties were obtained from DSC thermograms, recorded with a heat flux DSC822e instrument (Mettler-Toledo GmbH, Switzerland). The DSC822e was calibrated for temperature and enthalpy with a small piece of indium (melting point at 156.6° C.; ΔHf=28.45 J/g).

Figure 1B:
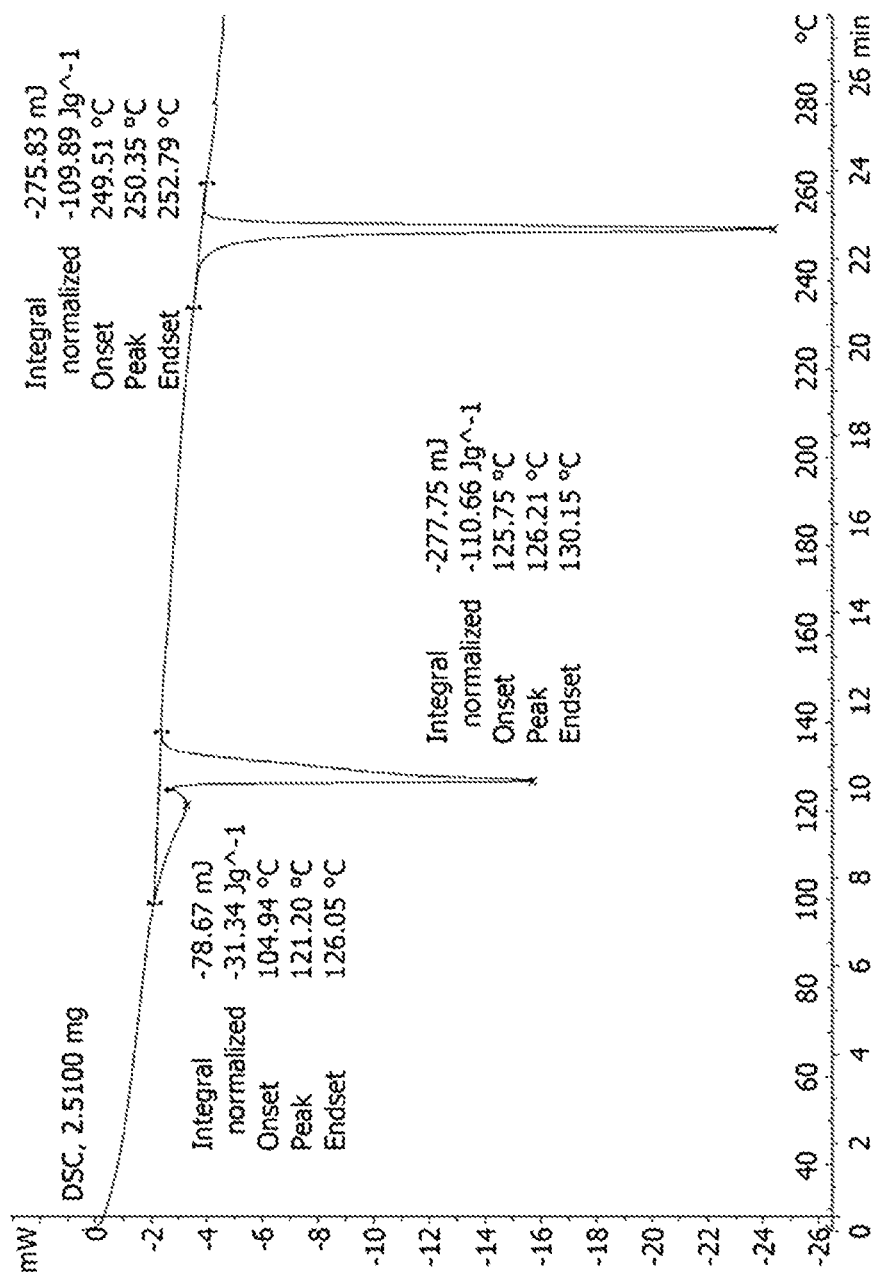
FIG. 1B shows a DSC curve of polymorph A.

Preferably, the DSC curve of the polymorph A corresponds to the DSC curve as shown in FIG. 1b.

The polymorph A of the present invention is preferably characterized by a Thermo-Gravimetric Analysis (TGA) thermogram showing an endothermic event between 240 and 250° C., more preferably between 242 and 248° C. and most preferably between 244 and 246° C. This endothermic event is attributed to the melting of anhydrous edaravone salt. Even more preferably, the TGA thermogram of the edaravone salt shows an additional endothermic event between 120 and 150° C. The latter endothermic event is attributed to the loss of hydrate water.

TGA is used to determine changes in weight in relation to change in temperature, which may reveal degradation of the compound and the presence of solvates. TGA analysis as described herein was carried out as follows: Approximately 1.5 mg of solid samples was weighed into 100 μL aluminum crucibles and sealed. The seals were pin-holed and the crucibles heated in the TGA from 25 to 300° C. at a heating rate of 10° C./min. Dry $N_2$ gas was used for purging. Mass loss due to solvent or water loss from the crystals was determined by TGA/SDTA. Monitoring the sample weight, during heating in a TGA/SDTA851e instrument (Mettler-Toledo GmbH, Switzerland), which resulted in a weight vs. temperature curve. The TGA/SDTA851e was calibrated with samples of indium and aluminum.

Figure 1C:
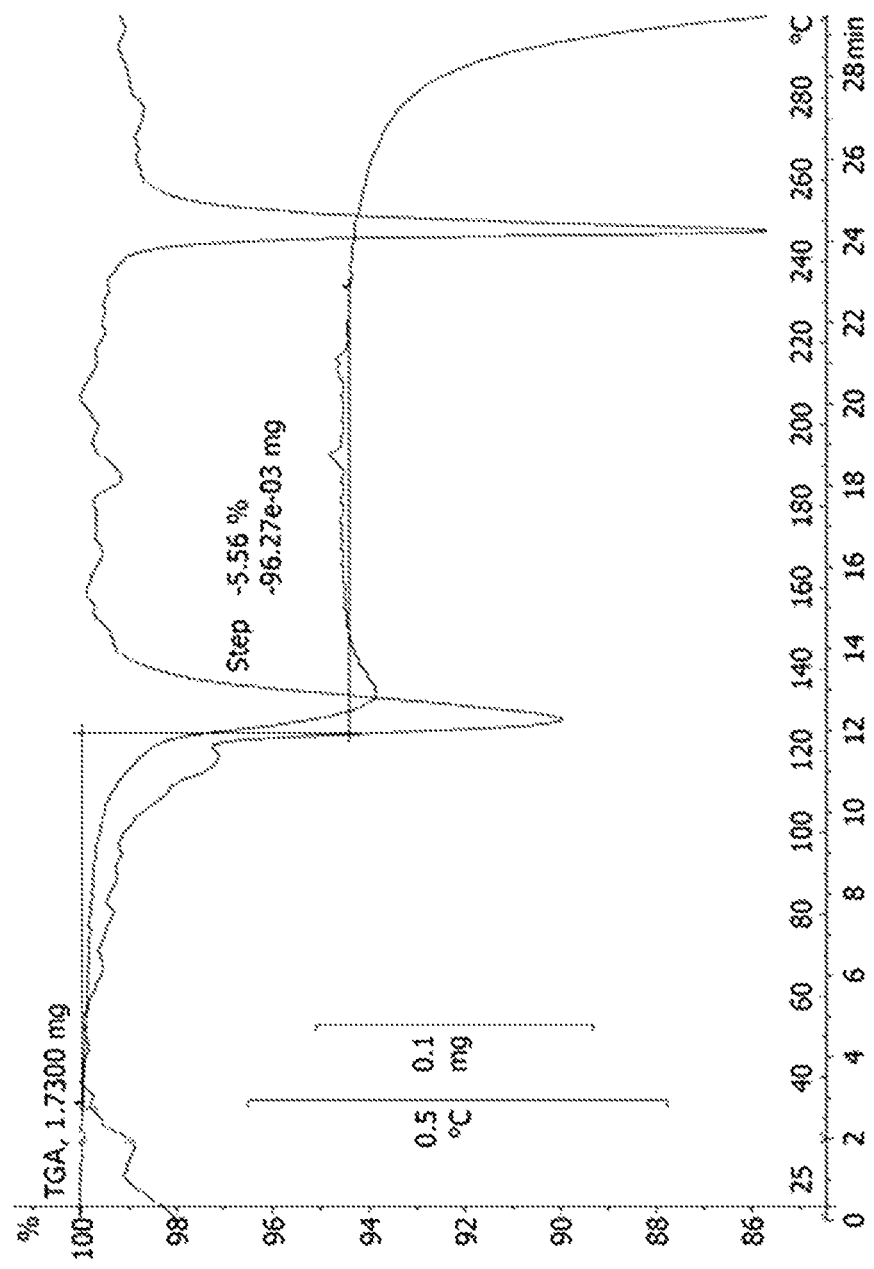
FIG. 1C shows a TGA curve of polymorph A.

Preferably, the polymorph A has a TGA curve that corresponds to the TGA curve as shown in FIG. 1c.

According to a particularly preferred embodiment, the single crystal structure of polymorph A corresponds to the single crystal structure that is shown in Tables 1 and 2 of the Examples.

Polymorph A of edaravone hemi-napadisylate monohydrate salt offers the advantage that is non-hygroscopic and very stable.

Edaravone Hemi-Napadisylate Monohydrate Salt—Polymorph B

The polymorph B edaravone salt of the present invention has an X-ray powder diffraction (XRPD) pattern comprising at least 8 peaks, more preferably at least 9 peaks and most preferably at least 10 peaks at diffraction angle 2-theta degrees that are within 0.1 degrees of 13.1, 14.5, 16.7, 19.5, 21.1, 21.8, 23.3, 23.6, 24.0, 25.6, 26.3 and 30.1 degrees.

According to another preferred embodiment, the XRPD pattern of polymorph B comprises at least 8 peaks, more preferably at least 9 peaks and most preferably at least 10 peaks at d-spacings that are within 0.05 Angstrom of 6.76, 6.12, 5.31, 4.56, 4.22, 4.07, 3.82, 3.76, 3.70, 3.48, 3.39 and 2.97 Angstroms.

The following table shows a typical XRPD peak list for the polymorph B.

| PEAK | ANGLE (2Θ) | D-SPACING | INTENSITY |
|---|---|---|---|
| 1 | 13.1 | 6.76 | 100 |
| 2 | 14.5 | 6.12 | 67 |
| 3 | 16.7 | 5.31 | 36 |
| 4 | 19.5 | 4.56 | 98 |
| 5 | 21.1 | 4.22 | 84 |
| 6 | 21.8 | 4.07 | 53 |
| 7 | 23.3 | 3.82 | 20 |
| 8 | 23.6 | 3.76 | 27 |
| 9 | 24.0 | 3.70 | 90 |
| 10 | 25.6 | 3.48 | 48 |
| 11 | 26.3 | 3.39 | 25 |
| 12 | 30.1 | 2.97 | 28 |

Figure 2A:
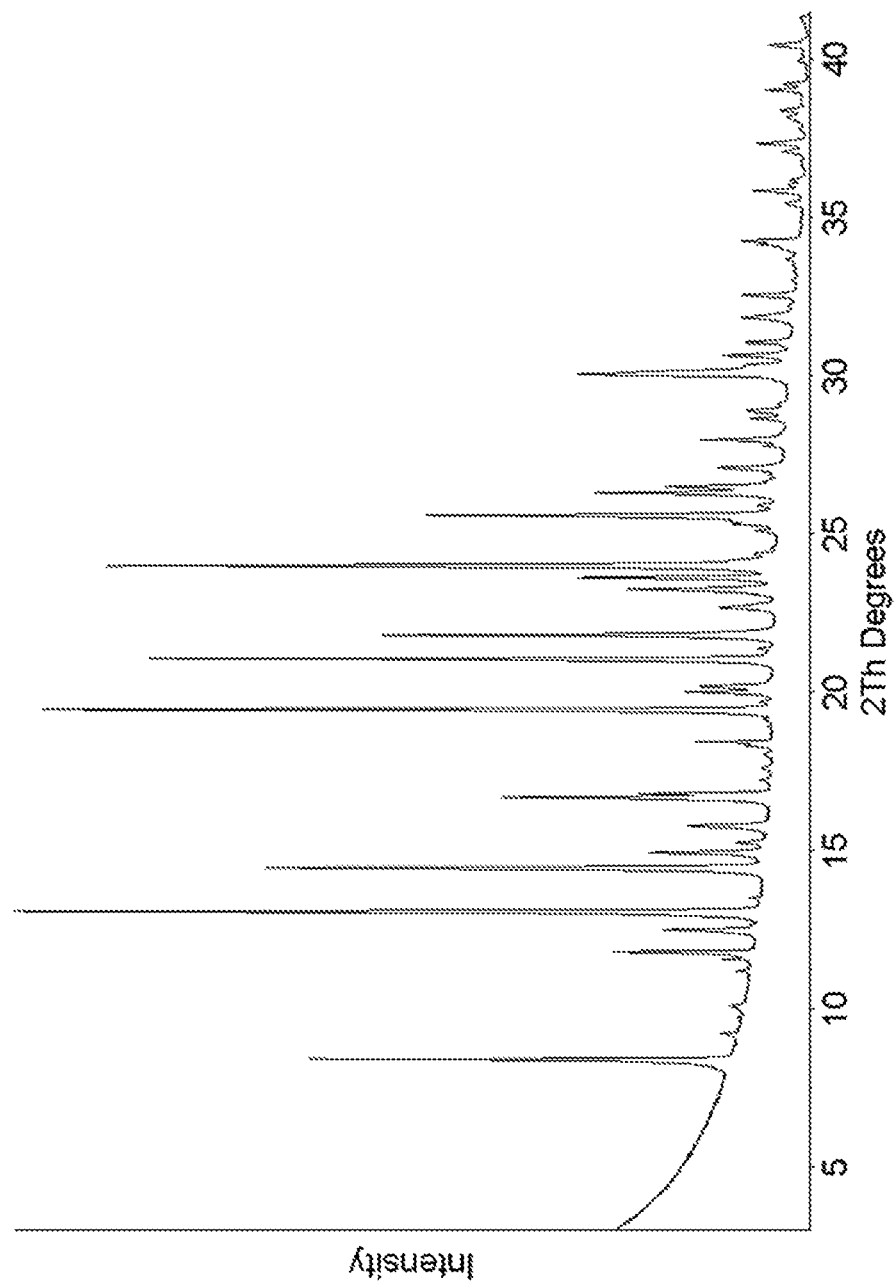
FIG. 2A shows an X-ray powder diffraction pattern of polymorph B.

The polymorph B preferably has a X-ray powder diffraction pattern that corresponds to the X-ray powder diffraction pattern shown in FIG. 2a.

The polymorph B of the present invention is preferably characterized by a differential scanning calorimetry (DSC) thermogram with an endothermic peak between 240 and 246° C. and/or between 250 and 255° C. These peaks are attributed to the melting of the anhydrous edaravone salts. Even more preferred, the DSC thermogram of the salt shows an additional endothermic peak between 125 and 132° C. The latter endothermic peak is deemed to correspond to the release of crystal water.

Figure 2B:
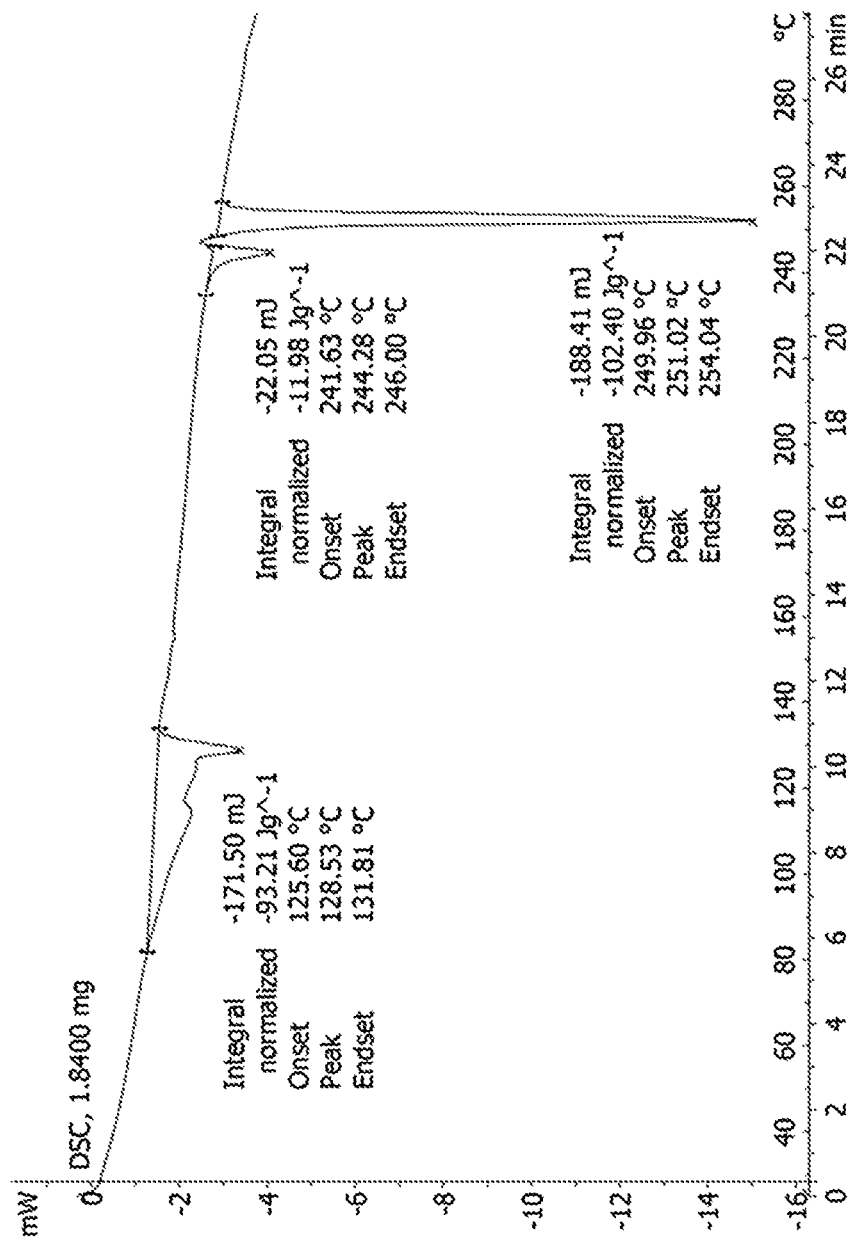
FIG. 2B shows a DSC curve of polymorph A.

Preferably, the DSC curve of the polymorph B corresponds to the DSC curve as shown in FIG. 2b.

The polymorph B of the present invention is preferably characterized by a Thermo-Gravimetric Analysis (TGA) thermogram showing an endothermic event between 240 and 250° C., more preferably between 242 and 248° C. and most preferably between 244 and 246° C. This endothermic event is attributed to the melting of anhydrous edaravone salt. Even more preferably, the TGA thermogram of the edaravone salt shows an additional endothermic event between 100 and 140° C. The latter endothermic event is attributed to the loss of hydrate water.

Figure 2C:
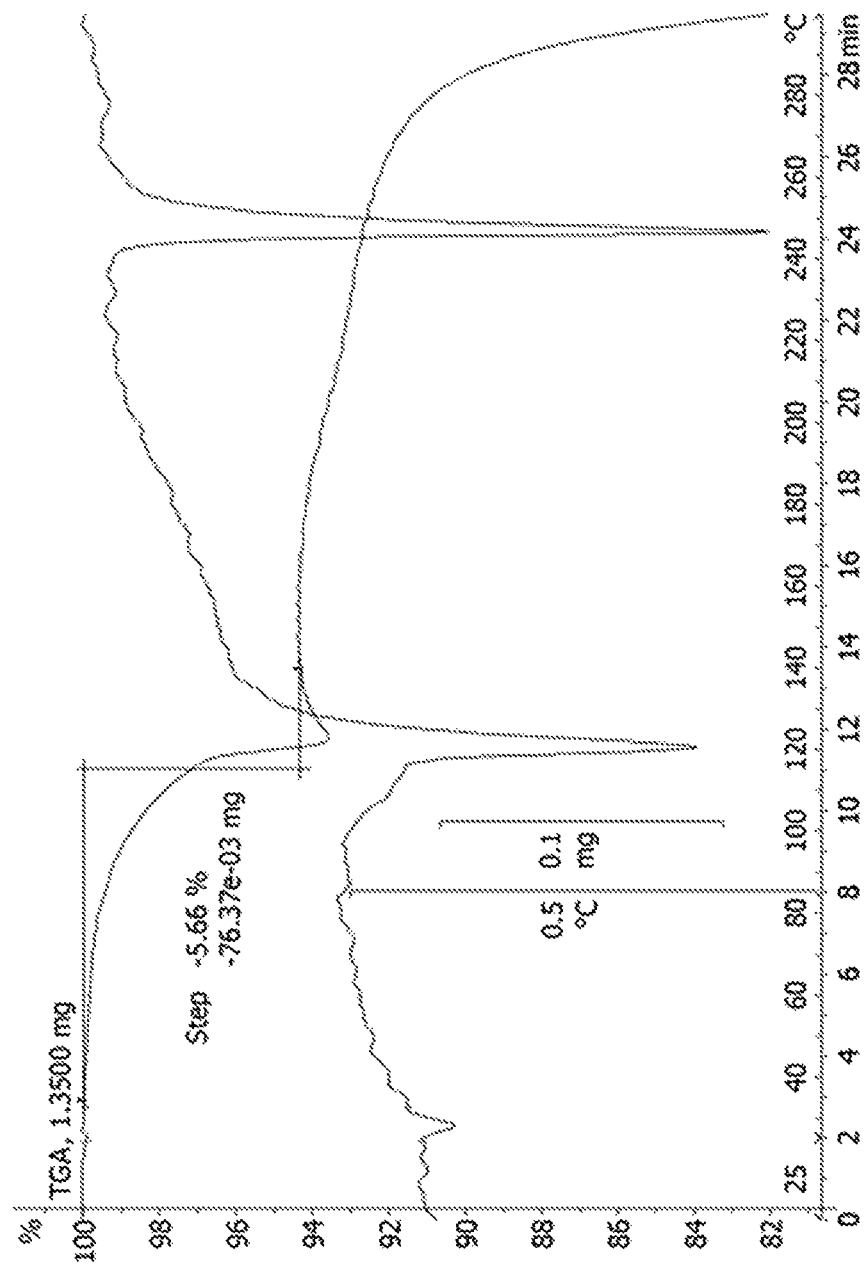
FIG. 2C shows a TGA curve of polymorph A.

Preferably, the polymorph B edaravone salt of the present invention has a TGA curve that corresponds to the TGA curve as shown in FIG. 2c.

Polymorph B of edaravone hemi-napadisylate monohydrate salt offers the advantage that is non-hygroscopic and very stable.

Edaravone Hemi-Napadisylate Monohydrate Salt—Polymorph C

According to a particularly preferred embodiment, the single crystal structure of polymorph C corresponds to the single crystal structure that is shown in Tables 1 and 2 of the Examples.

Edaravone Hemi-Napadisylate Hemi-Hydrate Salt—Polymorph D

The polymorph D edaravone salt of the present invention has an X-ray powder diffraction (XRPD) pattern comprising at least 8 peaks, more preferably at least 9 peaks and most preferably at least 10 peaks at diffraction angle 2-theta degrees that are within 0.1 degrees of 8.4, 11.6, 13.0, 13.6, 13.8, 17.1, 18.8, 19.1, 20.8, 22.6, 24.0, 24.4 and 26.1 degrees.

According to another preferred embodiment, the XRPD pattern of polymorph D comprises at least 8 peaks, more preferably at least 9 peaks and most preferably at least 10 peaks at d-spacings that are within 0.05 Angstrom of 10.54, 7.61, 6.82, 6.52, 6.43, 5.18, 4.71, 4.65, 4.27, 3.93, 3.71, 3.64 and 3.41 Angstroms.

The following table shows a typical XRPD peak list for the polymorph D.

| PEAK | ANGLE (2Θ) | D-SPACING | INTENSITY |
| --- | --- | --- | --- |
| 1 | 8.4 | 10.54 | 50 |
| 2 | 11.6 | 7.61 | 35 |
| 3 | 13.0 | 6.82 | 100 |
| 4 | 13.6 | 6.52 | 43 |
| 5 | 13.8 | 6.43 | 43 |
| 6 | 17.1 | 5.18 | 29 |
| 7 | 18.8 | 4.71 | 33 |
| 8 | 19.1 | 4.65 | 77 |
| 9 | 20.8 | 4.27 | 75 |
| 10 | 22.6 | 3.93 | 32 |
| 11 | 24.0 | 3.71 | 73 |
| 12 | 24.4 | 3.64 | 44 |
| 13 | 26.1 | 3.41 | 47 |

Figure 3A:
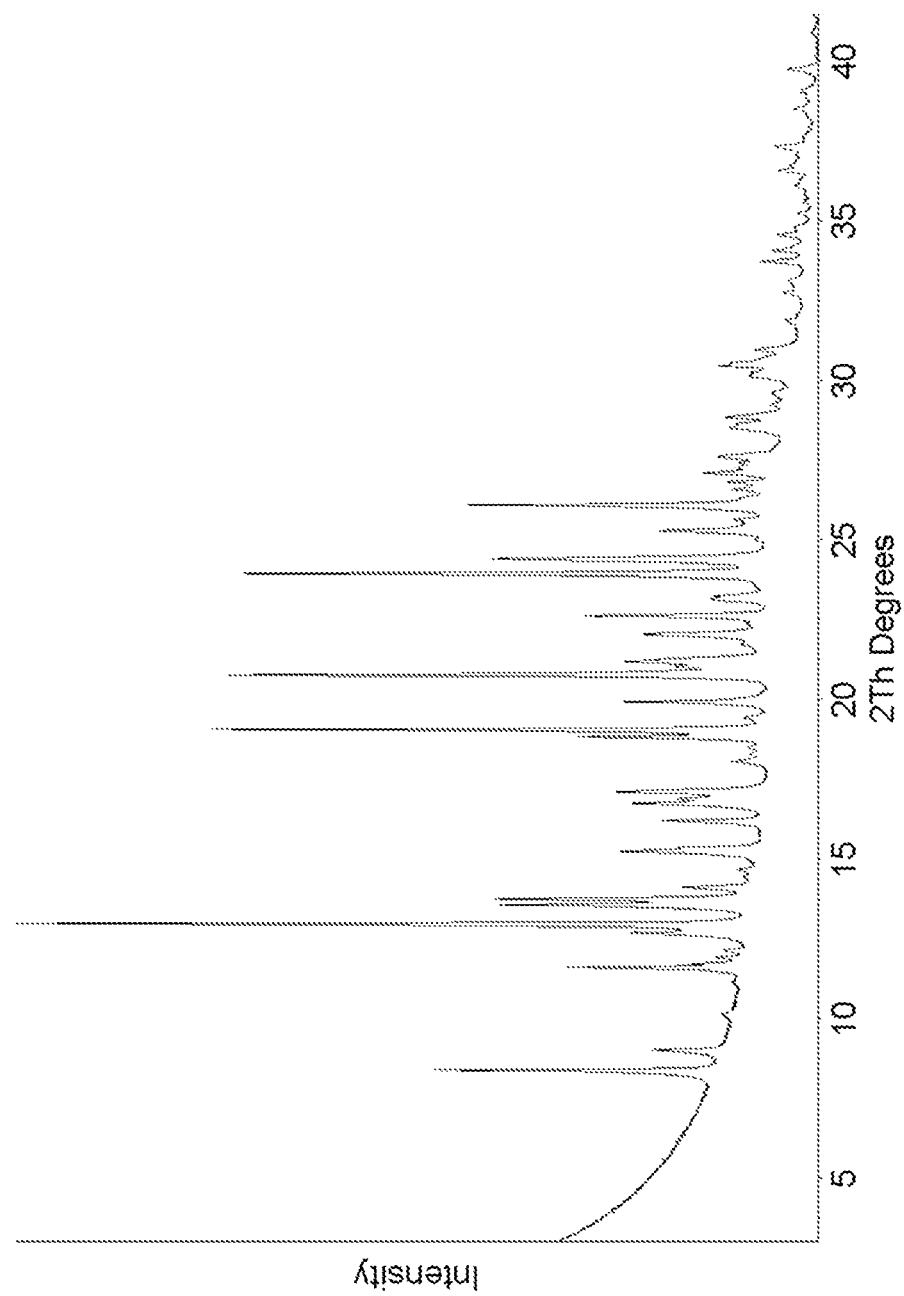
FIG. 3A shows an X-ray powder diffraction pattern of polymorph D.

The polymorph D preferably has a X-ray powder diffraction pattern that corresponds to the X-ray powder diffraction pattern shown in FIG. 3a.

The polymorph D of the present invention is preferably characterized by a differential scanning calorimetry (DSC) thermogram with an endothermic peak between 242 and 252° C. This peak is attributed to the melting of anhydrous edaravone salt.

Even more preferred, the DSC thermogram of the salt shows an additional endothermic peak between 40 and 95° C. The latter endothermic peak is deemed to correspond to the release of crystal water.

Figure 3B:
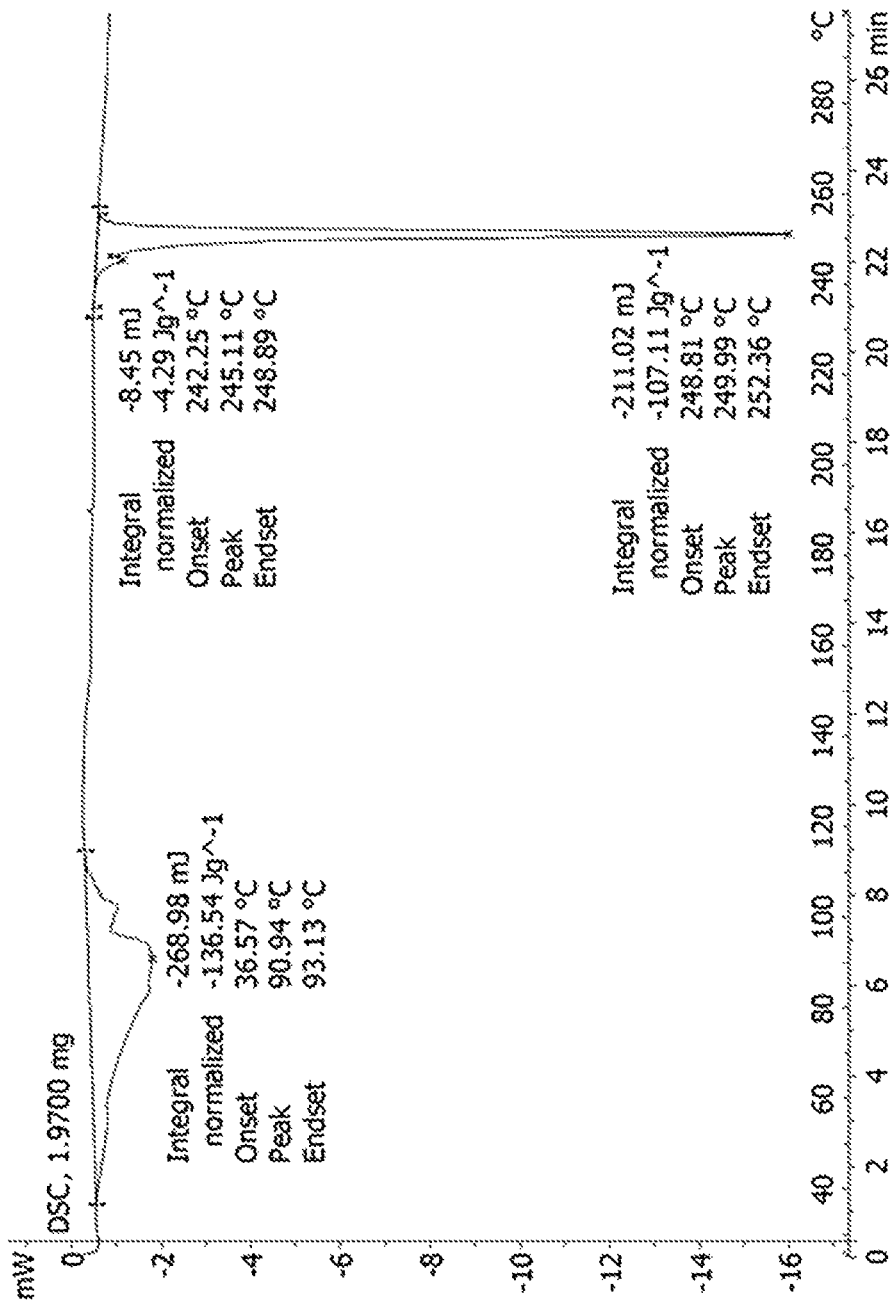
FIG. 3B shows a DSC curve of polymorph A.

Preferably, the DSC curve of the polymorph D corresponds to the DSC curve as shown in FIG. 3b.

The polymorph D of the present invention is preferably characterized by a Thermo-Gravimetric Analysis (TGA) thermogram showing an endothermic event between 240 and 260° C., more preferably between 242 and 255° C. and most preferably between 244 and 250° C. This endothermic event is attributed to the melting of anhydrous edaravone salt. Even more preferably, the TGA thermogram of the edaravone salt shows an additional endothermic event between 60 and 100° C. The latter endothermic event is attributed to the loss of hydrate water.

Figure 3C:
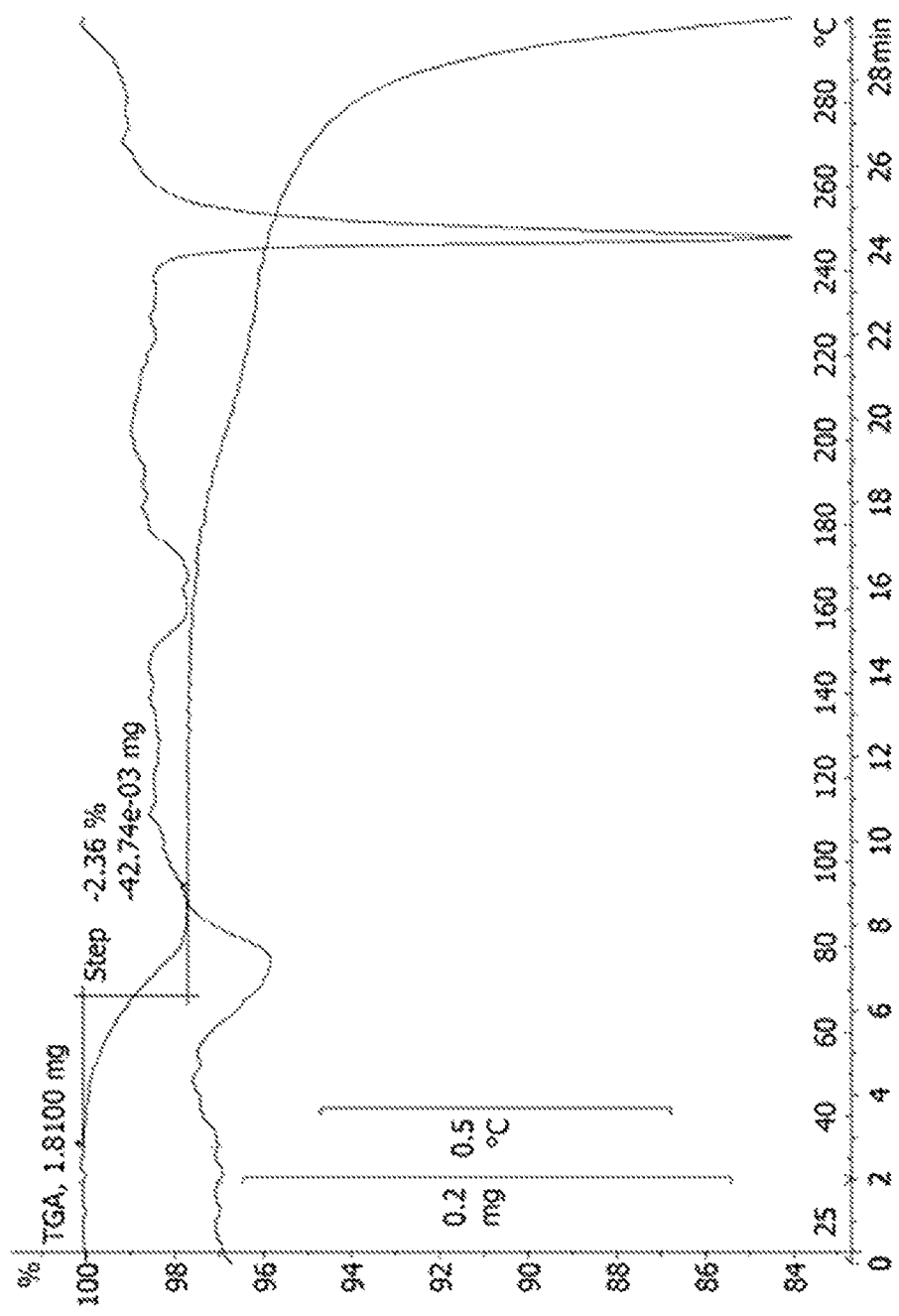
FIG. 3C shows a TGA curve of polymorph A.

Preferably, the polymorph D edaravone salt of the present invention has a TGA curve that corresponds to the TGA curve as shown in FIG. 3c.

Polymorph D of edaravone hemi-napadisylate monohydrate salt offers the advantage that it can easily be converted into polymorph B through absorption of water (at >50% RH).

Edaravone Hemi-Napadisylate Salt (Anhydrous)—Polymorph E

The polymorph E edaravone salt of the present invention has an X-ray powder diffraction (XRPD) pattern comprising at least 8 peaks, more preferably at least 8 peaks and most preferably at least 9 peaks at diffraction angle 2-theta degrees that are within 0.1 degrees of 10.2, 10.7, 11.1, 12.6, 16.2, 19.1, 19.4, 20.2, 21.7, 22.3 and 26.5 degrees.

According to another preferred embodiment, the XRPD pattern of polymorph E comprises at least 8 peaks, more preferably at least 9 peaks and most preferably at least 9 peaks at d-spacings that are within 0.05 Angstrom of 8.70, 8.25, 7.94, 7.02, 5.49, 4.66, 4.57, 4.39, 4.09, 3.98 and 3.36 Angstroms.

The following table shows a typical XRPD peak list for the polymorph C.

| PEAK | ANGLE (2Θ) | D-SPACING | INTENSITY |
| --- | --- | --- | --- |
| 1 | 10.2 | 8.70 | 91 |
| 2 | 10.7 | 8.25 | 22 |
| 3 | 11.1 | 7.94 | 41 |
| 4 | 12.6 | 7.02 | 43 |
| 5 | 16.2 | 5.49 | 47 |
| 6 | 19.1 | 4.66 | 100 |
| 7 | 19.4 | 4.57 | 22 |
| 8 | 20.2 | 4.39 | 21 |
| 9 | 21.7 | 4.09 | 47 |
| 10 | 22.3 | 3.98 | 38 |
| 11 | 26.5 | 3.36 | 43 |

Figure 4A:
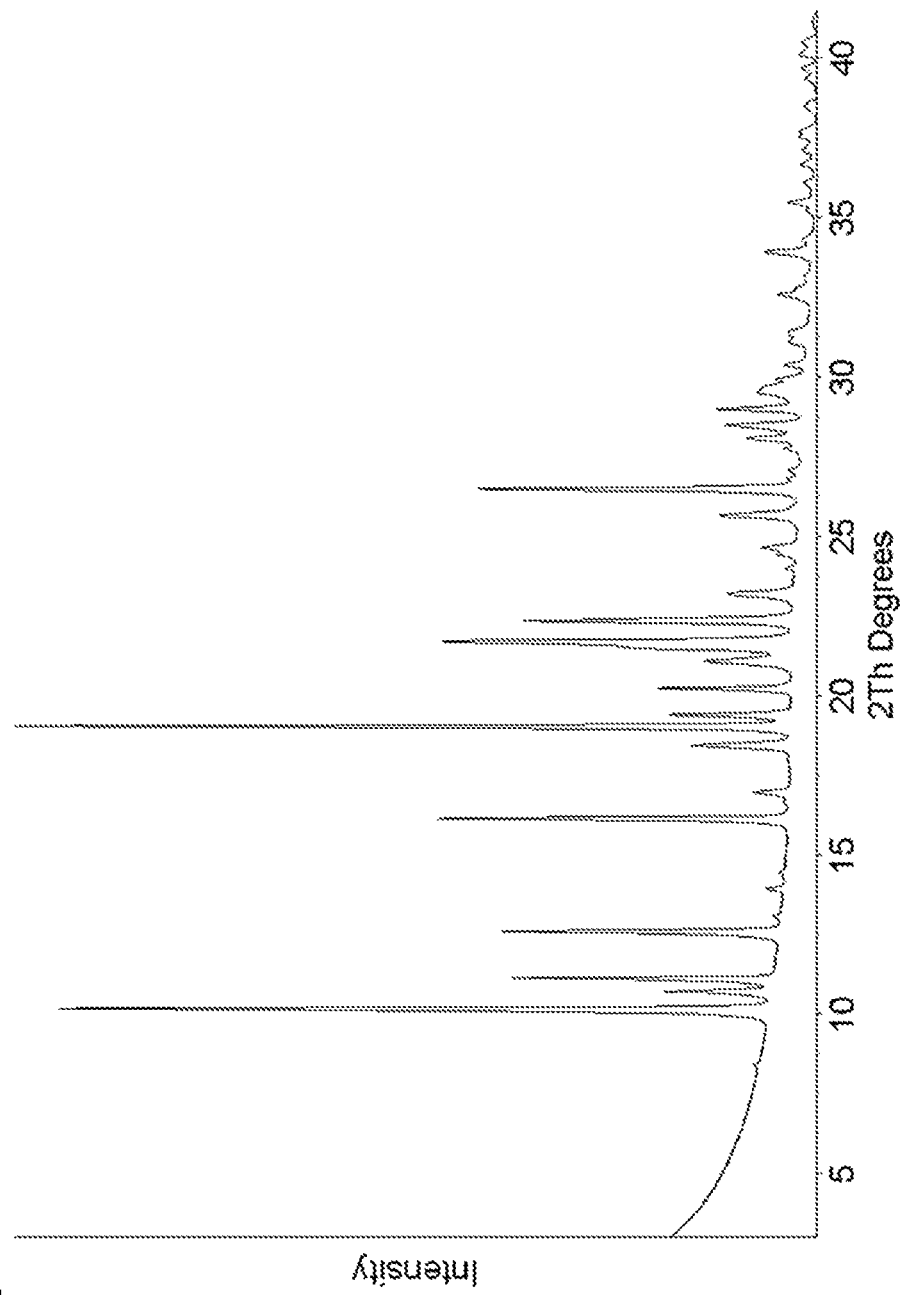
FIG. 4A shows an X-ray powder diffraction pattern of polymorph E.

The polymorph E preferably has a X-ray powder diffraction pattern that corresponds to the X-ray powder diffraction pattern shown in FIG. 4a.

The polymorph E of the present invention is preferably characterized by a differential scanning calorimetry (DSC) thermogram with an endothermic peak between 249 and 252° C. This peak is attributed to the melting of anhydrous edaravone salt.

Figure 4B:
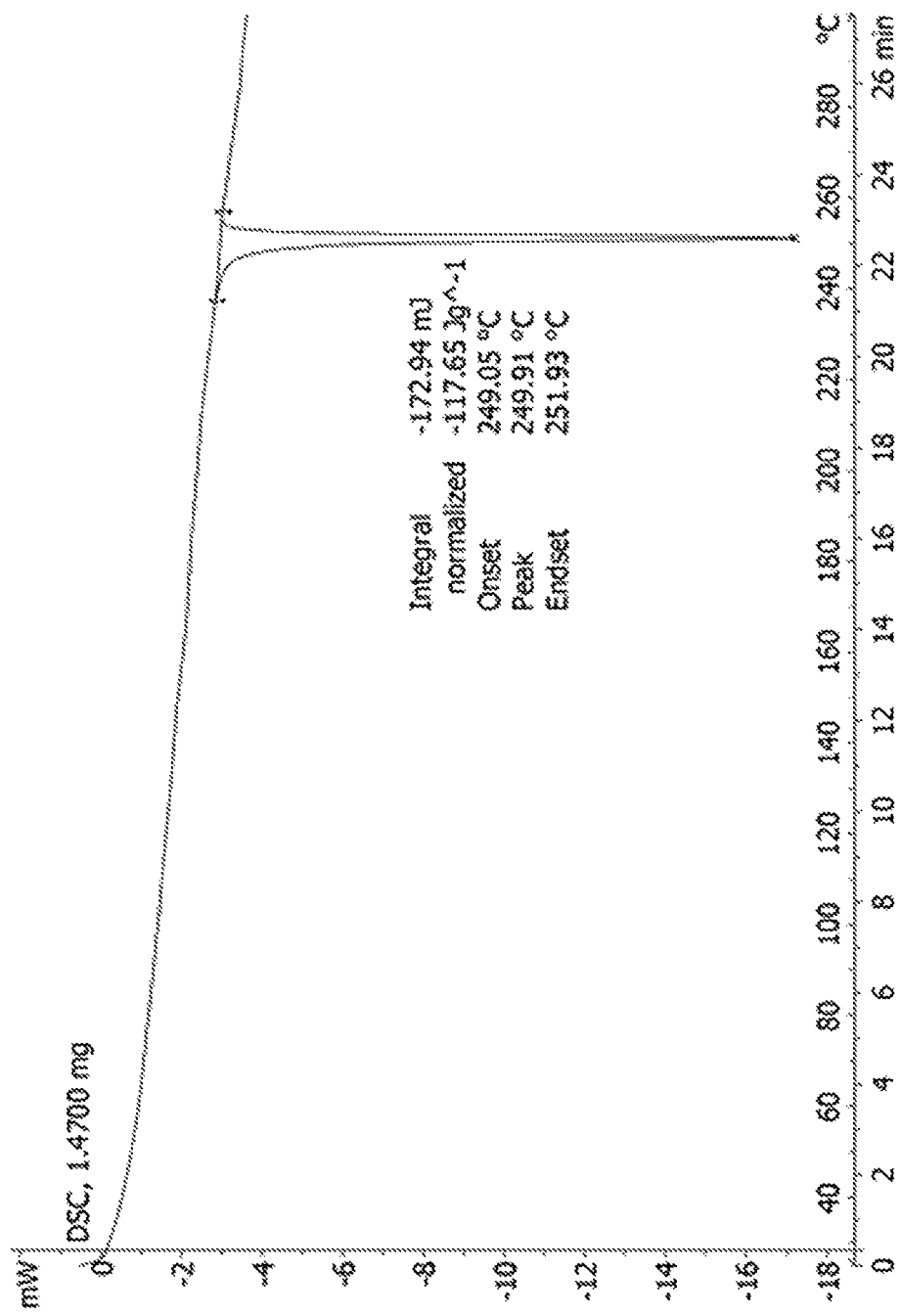
FIG. 4B shows a DSC curve of polymorph A.

Preferably, the DSC curve of the polymorph E corresponds to the DSC curve as shown in FIG. 4b.

The polymorph E of the present invention is preferably characterized by a Thermo-Gravimetric Analysis (TGA) thermogram showing an endothermic event between 240 and 252° C., more preferably between 242 and 250° C. and most preferably between 244 and 248° C. This endothermic event is attributed to the melting of the edaravone salt.

Figure 4C:
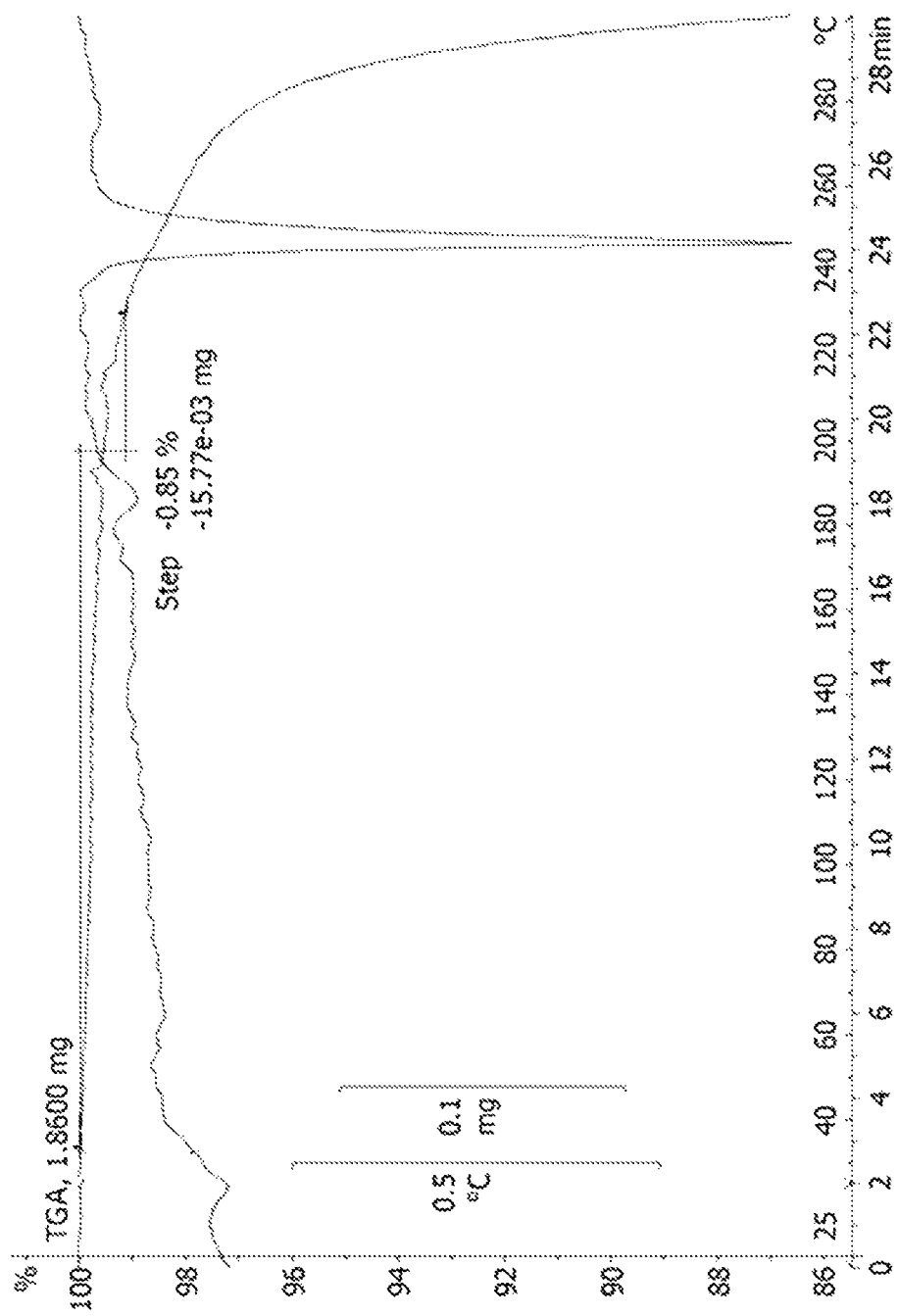
FIG. 4C shows a TGA curve of polymorph A.

Preferably, the polymorph E edaravone salt of the present invention has a TGA curve that corresponds to the TGA curve as shown in FIG. 4c.

Edaravone Hemi-Napadisylate Salt (Anhydrous)—Polymorph F

The polymorph F edaravone salt of the present invention has an X-ray powder diffraction (XRPD) pattern comprising at least 8 peaks, more preferably at least 9 peaks and most preferably at least 10 peaks at diffraction angle 2-theta degrees that are within 0.1 degrees of 11.54, 13.91, 14.09, 16.84, 18.25, 18.55, 19.11, 22.39, 22.76, 24.63 and 25.58 degrees.

According to another preferred embodiment, the XRPD pattern of polymorph F comprises at least 8 peaks, more preferably at least 9 peaks and most preferably at least 9 peaks at d-spacings that are within 0.05 Angstrom of 7.66, 6.36, 6.28, 5.26, 4.86, 4.78, 4.64, 3.97, 3.90, 3.61 and 3.48 Angstroms.

The following table shows a typical XRPD peak list for the polymorph F.

| PEAK | ANGLE (2Θ) | D-SPACING | INTENSITY |
| --- | --- | --- | --- |
| 1 | 11.54 | 7.66 | 100 |
| 2 | 13.91 | 6.36 | 29 |
| 3 | 14.09 | 6.28 | 21 |
| 4 | 16.84 | 5.26 | 33 |
| 5 | 18.25 | 4.86 | 30 |
| 6 | 18.55 | 4.78 | 47 |
| 7 | 19.11 | 4.64 | 28 |
| 8 | 22.39 | 3.97 | 54 |
| 9 | 22.76 | 3.90 | 21 |
| 10 | 24.63 | 3.61 | 59 |
| 11 | 25.58 | 3.48 | 71 |

Figure 5A:
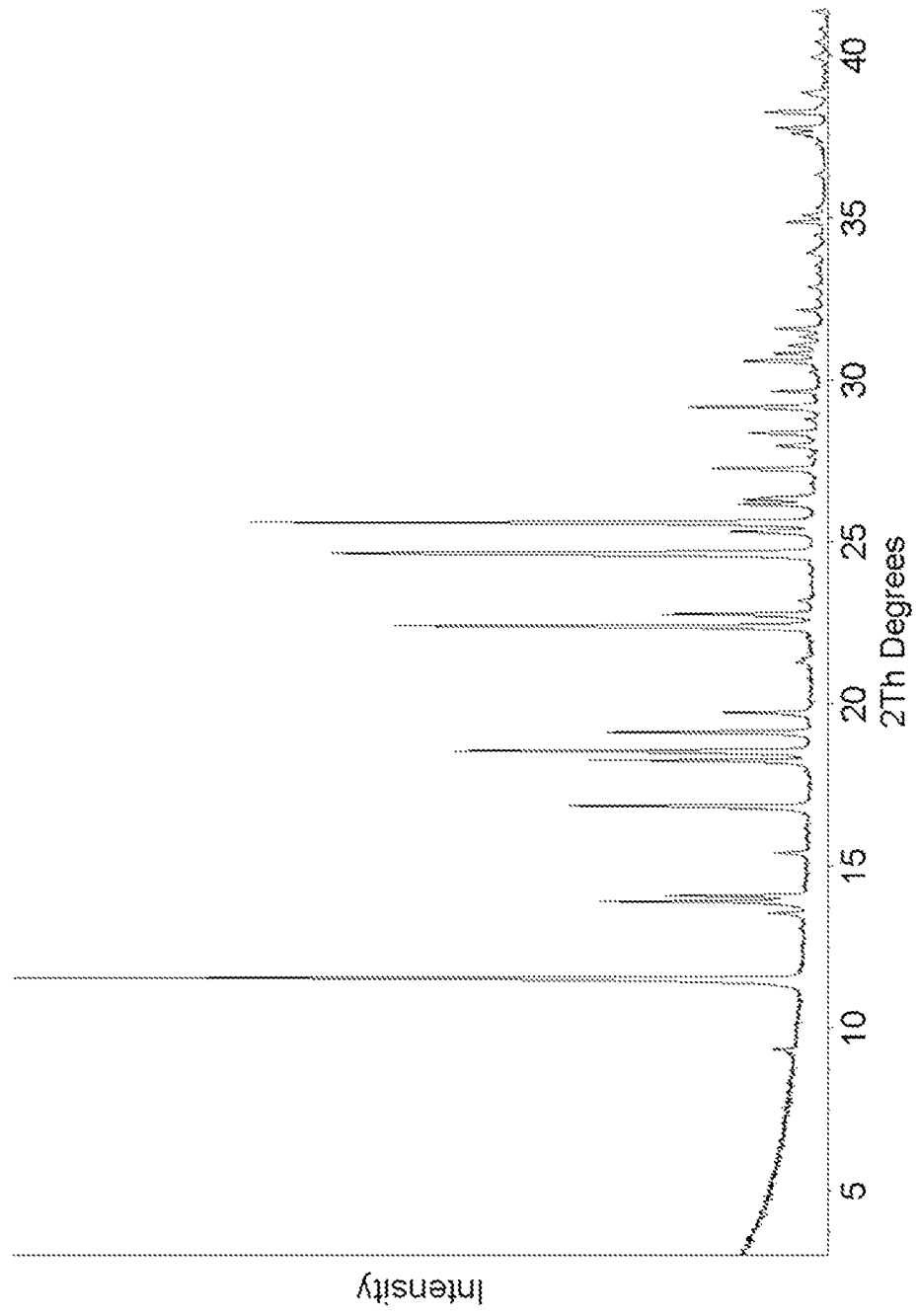
FIG. 5A shows an X-ray powder diffraction pattern of polymorph F.

The polymorph F preferably has a X-ray powder diffraction pattern that corresponds to the X-ray powder diffraction pattern shown in FIG. 5a.

The polymorph F of the present invention is preferably characterized by a differential scanning calorimetry (DSC) thermogram with an endothermic peak between 242 and 246° C. This peak is attributed to the melting of anhydrous edaravone salt. Even more preferred, the DSC thermogram of the salt shows an additional endothermic peak between 250 and 252° C. The latter endothermic peak is deemed to correspond to the melting of polymorph E.

Figure 5B:
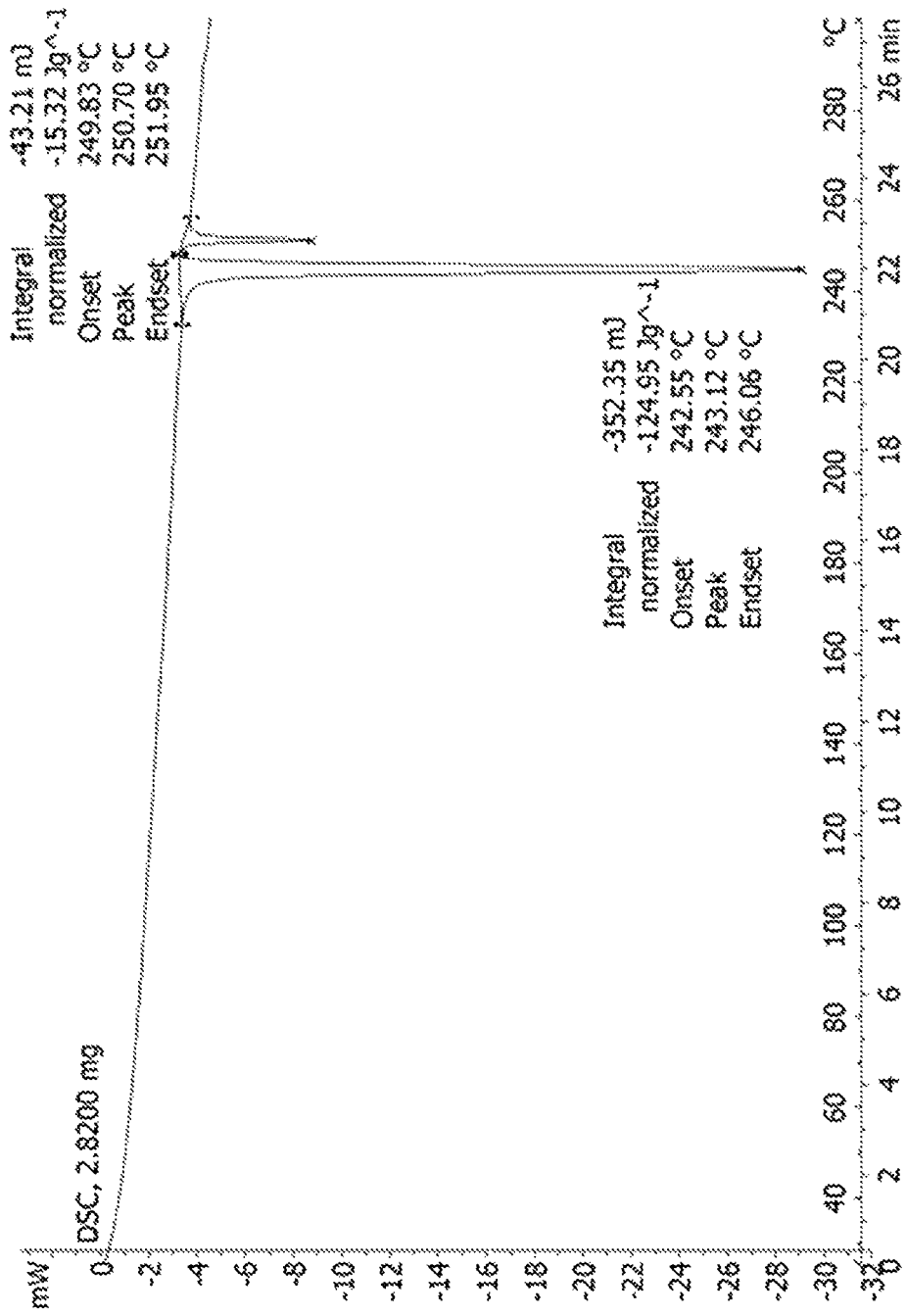
FIG. 5B shows a DSC curve of polymorph A.

Preferably, the DSC curve of the polymorph F corresponds to the DSC curve as shown in FIG. 5b.

The polymorph F of the present invention is preferably characterized by a Thermo-Gravimetric Analysis (TGA) thermogram showing an endothermic event between 235 and 258° C., more preferably between 237 and 256° C. and most preferably between 239 and 254° C. This endothermic event is attributed to the melting of the edaravone salt.

Figure 5C:
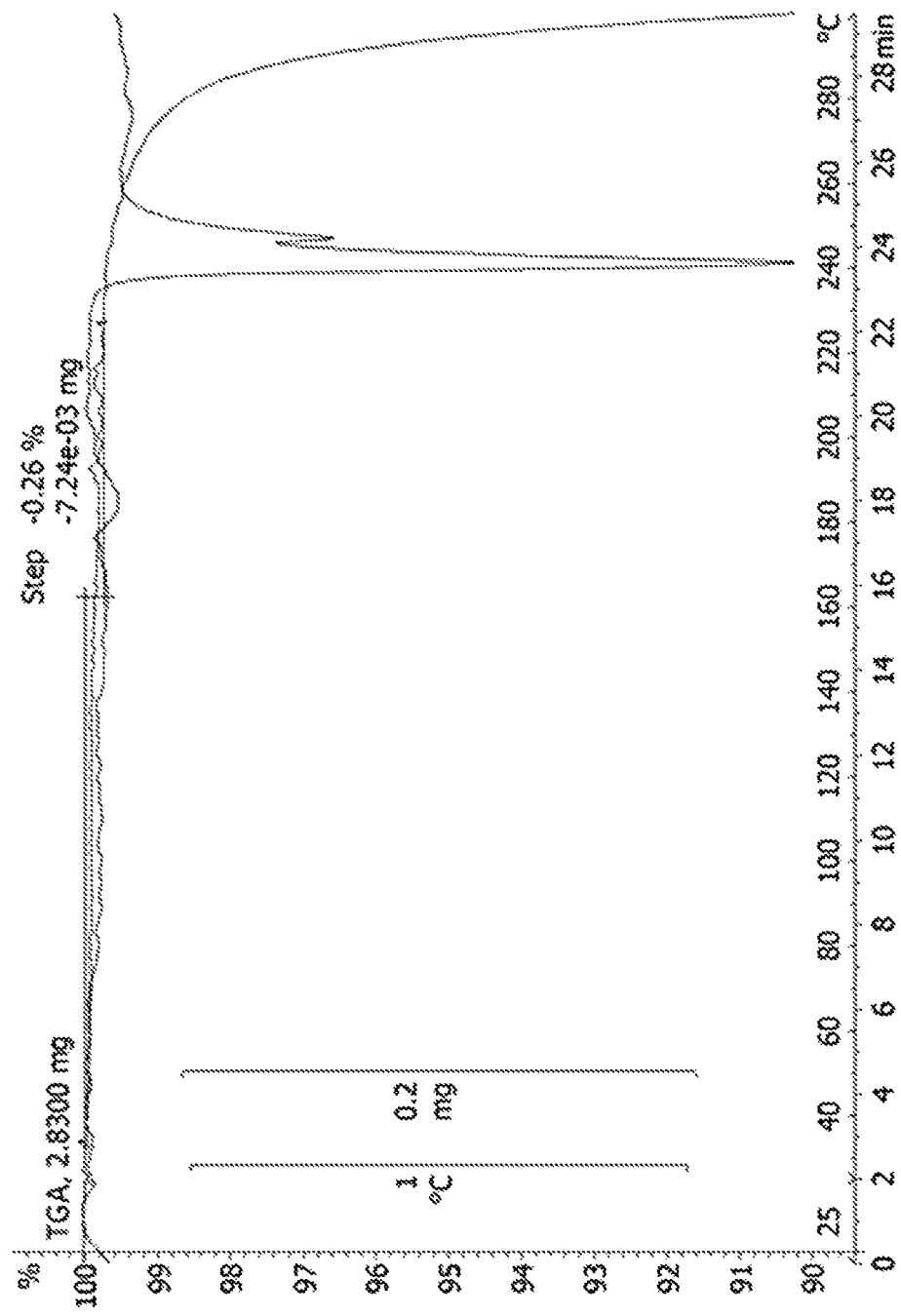
FIG. 5C shows a TGA curve of polymorph A.

Preferably, the polymorph F edaravone salt of the present invention has a TGA curve that corresponds to the TGA curve as shown in FIG. 5c.

Polymorph F of edaravone napadisylate monohydrate salt offers the that it can easily be converted into polymorph D through absorption of water (at >75% RH).

Another aspect of the present invention relates to a pharmaceutical composition comprising an edaravone salt according to the present invention.

Examples of pharmaceutical compositions encompassed by the present invention include solid compositions (e.g. tablets or powders), liquid compositions (e.g. solutions or suspensions) and semi-solid compositions (e.g. creams or gels).

According to a preferred embodiment, the pharmaceutical composition is an oral dosage unit. Examples of oral dosage units that are encompassed by the present invention include tablets, capsules and lozenges. Typically, the oral dosage unit contains the edaravone salt in a concentration of 50-1,000 mg/g edaravone salt, more preferably of 75-800 mg/g edaravone salt and most preferably 100-600 mg/g edaravone salt.

The oral dosage unit according to the present invention preferably has a weight of 50-5,000 mg, more preferably of 100-2,500 mg and most preferably of 200-1,500 mg.

The total amount of edaravone salt in the oral dosage unit preferably is in the range of 15-450 mg edaravone equivalent, more preferably in the range of 30-300 mg edaravone equivalent and most preferably in the range of 60-210 mg edaravone equivalent.

According to another preferred embodiment, the pharmaceutical composition is a powder (e.g. a granulate). Such a powder may be dissolved into aqueous liquid to prepare a liquid formulation that can be ingested or that can be gastrically administered. Preferably, this powder contains the edaravone salt in a concentration of 40-1,000 mg/g edaravone salt, more preferably of 75-800 mg/g edaravone salt and most preferably 100-600 mg/g edaravone salt.

According to yet another preferred embodiment the pharmaceutical composition is an aqueous liquid, more preferably a sterile aqueous liquid. Such an aqueous liquid may suitably be used to orally, gastrically or parentally administer the edaravone salt. Preferably, the aqueous liquid contains the edaravone salt in a concentration of 0.15-6 mg/g edaravone equivalent, more preferably of 0.25-5 mg/g edaravone equivalent and most preferably 0.4-4 mg/g edaravone equivalent.

According to a further preferred embodiment the pharmaceutical composition is a transdermal delivery system, such as a film or a patch. The transdermal delivery system preferably comprises a dispersion of the edaravone in a pharmaceutically acceptable matrix.

Yet another aspect of the present invention relates to the use of the pharmaceutical composition as described herein before in a treatment of a mammal, especially in a treatment of a human.

The present treatment preferably comprises therapeutic or palliative treatment.

The use of the pharmaceutical composition in a treatment preferably comprises enteric or parenteral administration of the composition. Examples of enteric administration include oral administration, gastric administration and rectal administration.

In a particularly preferred embodiment, the use comprises oral or gastric administration of the pharmaceutical composition to deliver a dose of 15-450 mg edaravone equivalent, more preferably of 30-300 mg edaravone equivalent and most preferably of 60-210 mg edaravone equivalent.

According to another preferred embodiment, the treatment according to the present invention comprises oral or gastric administration of the pharmaceutical composition to deliver 15-450 mg/day of edaravone equivalent, more preferably of 30-300 mg/day edaravone equivalent and most preferably 60-210 mg/day edaravone equivalent.

An alternative embodiment of the treatment according to the present invention comprises intravenous administration of the pharmaceutical composition to deliver a dose of 7-450 mg edaravone equivalent, preferably 15-250 mg edaravone equivalent and most preferably of 30-180 mg edaravone equivalent.

The treatment using intravenous administration preferably delivers 7-450 mg/day of edaravone equivalent, more preferably 15-250 mg/day edaravone equivalent and most preferably 30-180 mg/day edaravone equivalent.

The pharmaceutical composition of the present invention can suitably be used for the treatment of neurodegenerative diseases; cerebral amyloid angiopathy (CAA); auto-immune diseases; myocardial infarction; and cerebrovascular diseases.

Yet another aspect of the present invention relates to a method of preparing 3-methyl-1-phenyl-2-pyrazolin-5-one napadisylate or 3-methyl-1-phenyl-2-pyrazolin-5-one hemi-napadisylate, said method comprising:
  providing an edaravone solution containing 3-methyl-1-phenyl-2-pyrazolin-5-one in cationic form;
  combining the edaravone solution with napadisylate or napadisylate solute; and
  precipitating 3-methyl-1-phenyl-2-pyrazolin-5-one napadisylate and/or 3-methyl-1-phenyl-2-pyrazolin-5-one hemi-napadisylate.

The edaravone solution containing edaravone in cationic form preferably contains one or more solvents selected from acetonitrile, isopropanol, ethanol, methanol, ethyl acetate, tetrahydrofuran, toluene and mixtures thereof.

In a preferred embodiment, the precipitated 3-methyl-1-phenyl-2-pyrazolin-5-one napadisylate and/or the precipitated 3-methyl-1-phenyl-2-pyrazolin-5-one hemi-napadisylate is dried under vacuum.

The invention is further illustrated by the following non-limiting examples.

EXAMPLES

Example 1

A crystalline edaravone hemi-napadisylate monohydrate salt (polymorph A) was prepared as follows.

3-methyl-1-phenyl-2-pyrazolin-5-one (508 mg) was dissolved in 10.8 mL of acetonitrile at ambient conditions. To the resulting clear solution, 547.2 mg of 1,5-naphthalenedisulfonic acid dissolved in 1.5 mL of water was added. The solution was thermo-cycled between room temperature and 50° C. under continuous stirring. During the temperature cycle the salt crystallized. The solid fraction was filtered and dried under vacuum (ambient conditions, 5 mbar). A white crystalline substance was obtained.

$^1$H-NMR analysis showed that the crystalline edaravone salt was 3-methyl-1-phenyl-2-pyrazolin-5-one hemi-napadisylate monohydrate.

The crystalline substance was analysed by means of XRPD, DSC and TGA. The results of these analyses are shown in FIGS. 1a (XRPD), 1b (DSC) and 1c (TGA).

Single crystals of the edaravone salt were used to determine the crystal structure and cell parameters. The results are shown in Tables 1 and 2. Table 2 shows the atomic coordinates and equivalent isotropic displacement parameters. $U_{eq}$ is defined as one third of the trace of the orthogonalized Uij tensor.

The single crystal structure showed that the crystalline edaravone salt was 3-methyl-1-phenyl-2-pyrazolin-5-one hemi-napadisylate monohydrate.

TABLE 1

| | |
|---|---|
| Temperature | 296(2) K |
| λ [Å] | 0.71073 |
| Crystal system | Triclinic |
| Space group | P-1 |
| Unit cell dimensions | |
| a [Å] | 9.7390(3) |
| b [Å] | 9.7600(2) |
| c [Å] | 10.3732(3) |
| α [°] | 117.7875(16) |
| β [°] | 96.7748(15) |
| γ [°] | 108.2123(16) |
| V [Å$^3$] | 786.76(4) |
| Z | 2 |
| $D_c$ [gm/cm$^3$] | 1.420 |
| μ | 0.233 |
| F(000) | 352 |
| Crystal size [mm$^3$] | 0.28 × 0.16 × 0.12 |
| θ range for data collection [°] | 2.337 → 32.432. |
| Reflections collected | 13632 |
| Independent reflections | 5618 [$R_{int}$ = 0.0444] |
| Completeness to θ = 25.242° [%] | 99.3 |
| Absorption correction | Integration |
| Max. and min. transmission | 0.981 and 0.945 |
| Data/restraints/parameters | 5618/0/272 |
| Goodness-of-fit onF$^2$ | 1.025 |
| Final R indices [I > 2σ(I)] | R1 = 0.0481, wR2 = 0.1174 |
| R indices (all data) | R1 = 0.0647, wR2 = 0.1304 |
| Extinction coefficient | n/a |
| Largest diff. peak and hole [e/Å$^3$] | 0.288 and −0.412 |

TABLE 2

| | x | y | z | $U_{eq}$ or $U_{iso}$ |
|---|---|---|---|---|
| N1 | 0.59487(15) | 0.82745(15) | 0.52467(14) | 0.0414(3) |
| N2 | 0.46539(14) | 0.68754(16) | 0.48043(14) | 0.0404(3) |
| H2 | 0.452(2) | 0.585(3) | 0.413(2) | 0.055(5) |
| C3 | 0.37524(17) | 0.73541(19) | 0.56183(18) | 0.0414(3) |
| C4 | 0.2311(2) | 0.6063(3) | 0.5437(3) | 0.0595(5) |
| H4A | 0.168(4) | 0.654(4) | 0.587(4) | 0.106(9) |
| H4B | 0.249(4) | 0.558(5) | 0.597(4) | 0.144(14) |
| H4C | 0.181(5) | 0.538(5) | 0.450(5) | 0.151(15) |
| C5 | 0.44498(19) | 0.9108(2) | 0.66056(19) | 0.0458(3) |
| H5 | 0.407(2) | 0.981(3) | 0.735(2) | 0.059(6) |
| C6 | 0.58287(19) | 0.96492(18) | 0.63600(17) | 0.0425(3) |

TABLE 2-continued

| | x | y | z | $U_{eq}$ or $U_{iso}$ |
|---|---|---|---|---|
| O7 | 0.69606(16) | 1.11591(15) | 0.69717(16) | 0.0593(3) |
| H7 | 0.675(3) | 1.198(3) | 0.781(3) | 0.085(8) |
| C8 | 0.72754(17) | 0.81032(17) | 0.48561(16) | 0.0376(3) |
| C9 | 0.8566(2) | 0.8707(2) | 0.60197(18) | 0.0473(3) |
| H9A | 0.853(3) | 0.927(3) | 0.707(3) | 0.072(6) |
| C10 | 0.9839(2) | 0.8526(2) | 0.5655(2) | 0.0537(4) |
| H10 | 1.072(3) | 0.892(3) | 0.639(2) | 0.061(6) |
| C11 | 0.9816(2) | 0.7737(2) | 0.4142(2) | 0.0547(4) |
| H11 | 1.070(3) | 0.768(3) | 0.390(2) | 0.068(6) |
| C12 | 0.8514(2) | 0.7135(2) | 0.2991(2) | 0.0567(4) |
| H12 | 0.850(3) | 0.660(3) | 0.194(3) | 0.083(7) |
| C13 | 0.7229(2) | 0.7318(2) | 0.33368(18) | 0.0478(4) |
| H13 | 0.632(3) | 0.696(3) | 0.257(2) | 0.065(6) |
| O21 | 0.39584(13) | 0.36048(13) | 0.27039(12) | 0.0481(3) |
| O22 | 0.49962(13) | 0.22013(14) | 0.07246(15) | 0.0492(3) |
| O23 | 0.34820(15) | 0.35954(15) | 0.03557(15) | 0.0525(3) |
| S24 | 0.37645(4) | 0.26957(4) | 0.10678(4) | 0.03550(10) |
| C25 | 0.20981(15) | 0.07703(15) | 0.02664(14) | 0.0322(2) |
| C26 | 0.22783(17) | −0.07206(17) | −0.03026(17) | 0.0396(3) |
| H26A | 0.323(2) | −0.073(2) | −0.035(2) | 0.045(5) |
| C27 | 0.10122(19) | −0.22682(18) | −0.0874(2) | 0.0449(3) |
| H27 | 0.119(2) | −0.331(3) | −0.125(2) | 0.056(5) |
| C29 | 0.06411(15) | 0.07902(15) | 0.02886(14) | 0.0312(2) |
| O30 | 0.65389(19) | 0.34187(17) | −0.08483(18) | 0.0639(4) |
| H30A | 0.647(3) | 0.429(4) | −0.077(3) | 0.098(9) |
| H30B | 0.604(3) | 0.312(3) | −0.031(3) | 0.078(7) |
| C28 | −0.03995(17) | −0.23071(17) | −0.08681(17) | 0.0395(3) |
| H28 | −0.131(2) | −0.337(3) | −0.119(2) | 0.057(5) |

The edaravone salt was kept for 28 days at 40° C. and 75% RH without showing significant degradation.

The solubility of the edaravone salt in water was 2.8 and 3.2 mg/mL after 7 hours equilibration, whereas the freebase of edaravone had a solubility between 2.0 and 3.0 mg/mL after 7 hours equilibration. The intrinsic dissolution rate in water of the edaravone salt was 0.37 mg/min/cm$^2$, whereas the dissolution rate of the freebase was 0.22 mg/min/cm$^2$.

Example 2

A crystalline edaravone hemi-napadisylate monohydrate salt (polymorph C) was prepared as follows.

3-methyl-1-phenyl-2-pyrazolin-5-one (40 mg) was dissolved in 850 μL of acetonitrile at ambient conditions. To the resulting clear solution, 93.2 mg of 1,5-naphthalenedisulfonic acid dissolved in 250 μL of water was added. The solution was heated to 60° C. followed by cooling to 5° C. without stirring. During aging at 5° C. single crystals were crystallized. The crystals were collected by filtration.

Single crystals of the edaravone salt were used to determine the crystal structure and cell parameters. The results are shown in Tables 3 and 4. Table 4 shows the atomic coordinates and equivalent isotropic displacement parameters. $U_{eq}$ is defined as one third of the trace of the orthogonalized Uij tensor.

The single crystal structure showed that the crystalline edaravone salt was 3-methyl-1-phenyl-2-pyrazolin-5-one hemi-napadisylate monohydrate.

TABLE 3

| | |
|---|---|
| Temperature | 296(2) K |
| λ [Å] | 0.71073 |
| Crystal system | Orthorhombic |
| Space group | P2$_1$2$_1$2$_1$ |
| Unit cell dimensions | |
| a [Å] | 7.9705(6) |
| b [Å] | 18.8542(12) |

TABLE 3-continued

| | |
|---|---|
| c [Å] | 20.7017(12) |
| V [Å$^3$] | 3111.0(4) |
| Z | 8 |
| D$_c$ [gm/cm$^3$] | 1.436 |
| μ | 0.236 |
| F(000) | 1408 |
| Crystal size [mm$^3$] | 0.25 × 0.18 × 0.15 |
| θ range for data collection [°] | 2.2 → 32.5 |
| Reflections collected | 23655 |
| Independent reflections | 10907 [R$_{int}$ = 0.0600] |
| Completeness to θ = 25.242° [%] | 98.9 |
| Absorption correction | Integration |
| Max. and min. transmission | 0.985 and 0.958 |
| Data/restraints/parameters | 10907/0/521 |
| Goodness-of-fit on F$^2$ | 1.029 |
| Final R indices [I > 2σ(I)] | R1 = 0.0649, wR2 = 0.1115 |
| R indices (all data) | R1 = 0.1278, wR2 = 0.1397 |
| Absolute structure parameter | 0.01(5) |
| Extinction coefficient | n/a |
| Largest diff. peak and hole [e/Å$^3$] | 0.260 and −0.399 |

TABLE 4

| | x | y | z | U$_{eq}$ or U$_{iso}$ |
|---|---|---|---|---|
| N1 | 0.9163(5) | 0.6370(2) | 0.74158(17) | 0.0442(8) |
| N2 | 0.8932(5) | 0.6686(2) | 0.68250(19) | 0.0432(9) |
| H2A | 0.852(7) | 0.648(3) | 0.647(3) | 0.067(17) |
| C3 | 0.9546(6) | 0.7346(2) | 0.6845(2) | 0.0419(10) |
| C4 | 0.9459(8) | 0.7816(3) | 0.6276(3) | 0.0650(16) |
| H4A | 1.0007 | 0.8257 | 0.6371 | 0.098 |
| H4B | 0.8306 | 0.7904 | 0.6168 | 0.098 |
| H4C | 1.0008 | 0.7592 | 0.5917 | 0.098 |
| C5 | 1.0188(7) | 0.7467(3) | 0.7454(2) | 0.0454(11) |
| H5A | 1.075(6) | 0.786(3) | 0.761(2) | 0.041(13) |
| C6 | 0.9938(6) | 0.6847(3) | 0.7803(2) | 0.0446(11) |
| O7 | 1.0330(5) | 0.6681(2) | 0.83991(17) | 0.0605(10) |
| H7 | 1.079(10) | 0.705(4) | 0.861(4) | 0.11(3) |
| C8 | 0.8602(6) | 0.5660(3) | 0.7531(2) | 0.0449(11) |
| C9 | 0.8110(7) | 0.5462(3) | 0.8152(3) | 0.0568(13) |
| H9A | 0.819(7) | 0.580(3) | 0.851(2) | 0.058(16) |
| C10 | 0.7521(8) | 0.4783(4) | 0.8250(4) | 0.0710(18) |
| H10A | 0.722(7) | 0.462(3) | 0.866(3) | 0.068(18) |
| C11 | 0.7408(9) | 0.4308(4) | 0.7742(4) | 0.080(2) |
| H11 | 0.699(8) | 0.383(4) | 0.780(3) | 0.10(2) |
| C12 | 0.7913(9) | 0.4513(3) | 0.7130(4) | 0.0754(19) |
| H12A | 0.783(7) | 0.419(3) | 0.676(3) | 0.073(18) |
| C13 | 0.8524(8) | 0.5183(3) | 0.7020(3) | 0.0595(14) |
| H13A | 0.900(7) | 0.534(3) | 0.658(3) | 0.064(16) |
| N21 | 0.9245(5) | 0.8610(2) | 0.23104(17) | 0.0439(8) |
| N22 | 1.0038(5) | 0.8387(2) | 0.17523(19) | 0.0437(9) |
| H22A | 0.995(7) | 0.866(3) | 0.142(2) | 0.060(15) |
| C23 | 1.0624(6) | 0.7729(2) | 0.1833(2) | 0.0432(10) |
| C24 | 1.1514(8) | 0.7352(3) | 0.1309(2) | 0.0594(14) |
| H24A | 1.2641 | 0.7249 | 0.1444 | 0.089 |
| H24B | 1.1541 | 0.7645 | 0.093 | 0.089 |
| H24C | 1.094 | 0.6917 | 0.1213 | 0.089 |
| C25 | 1.0247(7) | 0.7519(3) | 0.2453(2) | 0.0457(12) |
| H25A | 1.048(6) | 0.712(3) | 0.265(2) | 0.042(14) |
| C26 | 0.9363(6) | 0.8071(3) | 0.2736(2) | 0.0433(11) |
| O27 | 0.8663(5) | 0.8136(2) | 0.33083(17) | 0.0586(10) |
| H27 | 0.894(8) | 0.770(3) | 0.353(3) | 0.08(2) |
| C28 | 0.8587(6) | 0.9315(3) | 0.2373(2) | 0.0451(11) |
| C29 | 0.8617(9) | 0.9644(3) | 0.2968(3) | 0.0658(16) |
| H29A | 0.914(7) | 0.939(3) | 0.331(3) | 0.065(17) |
| C30 | 0.7987(10) | 1.0316(4) | 0.3024(4) | 0.082(2) |
| H30A | 0.804(7) | 1.056(3) | 0.344(3) | 0.072(18) |
| C31 | 0.7370(9) | 1.0671(3) | 0.2495(4) | 0.0748(19) |
| H31A | 0.693(8) | 1.114(4) | 0.255(3) | 0.09(2) |
| C32 | 0.7353(8) | 1.0339(3) | 0.1907(4) | 0.0700(17) |
| H32A | 0.703(7) | 1.060(3) | 0.155(2) | 0.059(16) |
| C33 | 0.7942(7) | 0.9658(3) | 0.1839(3) | 0.0573(14) |
| H33A | 0.800(7) | 0.945(3) | 0.145(3) | 0.066(17) |
| O41 | 0.7431(4) | 0.61231(18) | 0.57835(16) | 0.0543(9) |
| O42 | 0.7545(4) | 0.61813(17) | 0.46222(15) | 0.0475(8) |
| O43 | 0.6270(4) | 0.71375(15) | 0.52219(17) | 0.0476(8) |
| S44 | 0.66194(12) | 0.63813(6) | 0.51998(5) | 0.0353(2) |

TABLE 4-continued

| | x | y | z | U$_{eq}$ or U$_{iso}$ |
|---|---|---|---|---|
| C45 | 0.4654(5) | 0.5937(2) | 0.5158(2) | 0.0327(8) |
| C46 | 0.3217(5) | 0.6334(2) | 0.5199(2) | 0.0382(9) |
| H46A | 0.330(6) | 0.682(3) | 0.523(2) | 0.053(14) |
| C47 | 0.1645(6) | 0.6003(2) | 0.5190(2) | 0.0430(10) |
| H47A | 0.067(7) | 0.626(3) | 0.521(3) | 0.068(16) |
| C48 | 0.1511(5) | 0.5291(2) | 0.5141(2) | 0.0404(10) |
| H48A | 0.043(6) | 0.506(2) | 0.516(2) | 0.057(15) |
| C49 | 0.2955(4) | 0.4851(2) | 0.50838(19) | 0.0314(8) |
| C50 | 0.2887(4) | 0.41004(19) | 0.5009(2) | 0.0312(8) |
| S51 | 0.09276(11) | 0.36448(5) | 0.49844(5) | 0.0345(2) |
| O52 | −0.0024(4) | 0.39577(16) | 0.44499(15) | 0.0434(7) |
| O53 | 0.0127(4) | 0.37656(17) | 0.56033(15) | 0.0460(8) |
| O54 | 0.1311(4) | 0.28988(15) | 0.48749(16) | 0.0457(8) |
| C55 | 0.4323(4) | 0.3701(2) | 0.4957(2) | 0.0350(8) |
| H55A | 0.428(6) | 0.317(3) | 0.489(2) | 0.061(15) |
| C56 | 0.5909(5) | 0.4028(2) | 0.4979(2) | 0.0406(10) |
| H56A | 0.691(5) | 0.375(2) | 0.497(2) | 0.047(12) |
| C57 | 0.6026(5) | 0.4744(2) | 0.5054(2) | 0.0382(9) |
| H57A | 0.710(5) | 0.4964(19) | 0.5067(19) | 0.032(11) |
| C58 | 0.4587(4) | 0.51806(19) | 0.5099(2) | 0.0310(8) |
| O61 | 0.9588(6) | 0.7049(2) | 0.39202(19) | 0.0596(11) |
| H61A | 0.900(7) | 0.681(3) | 0.407(3) | 0.049(17) |
| H61B | 1.027(16) | 0.728(5) | 0.430(5) | 0.20(5) |
| O62 | 1.1882(5) | 0.7718(2) | 0.88851(19) | 0.0502(9) |
| H62A | 1.125(9) | 0.803(3) | 0.903(3) | 0.08(2) |
| H62B | 1.252(10) | 0.758(3) | 0.914(3) | 0.09(3) |

Example 3

A crystalline edaravone hemi-napadisylate hemihydrate salt (polymorph D) was prepared as follows.

3-methyl-1-phenyl-2-pyrazolin-5-one (381 mg) was dissolved in 3.5 mL of acetonitrile at ambient conditions. To the resulting clear solution, 404 mg of 1,5-naphthalenedisulfonic acid dissolved in 1 mL of water was added. The solution was freeze-dried and the resulting solid was thermo-cycled in methanol/water (97/3, v/v) between room temperature and 50° C. under continuous stirring. During the temperature cycle the salt crystallized. The solid fraction was filtered and dried under vacuum (60° C., 5 mbar). A white crystalline substance was obtained.

$^1$H-NMR analysis showed that the crystalline edaravone salt was 3-methyl-1-phenyl-2-pyrazolin-5-one hemi-napadisylate hemihydrate.

The crystalline substance was analysed by means of XRPD, DSC and TGA. The results of these analyses are shown in FIGS. 4a (XRPD), 4b (DSC) and 4c (TGA).

The edaravone salt was kept for 28 days at 25° C. and 0% RH without showing any signs of degradation.

Example 4

A crystalline edaravone hemi-napadisylate monohydrate salt (polymorph B) was prepared by exposing the edaravone hemi-napadisylate hemihydrate salt of Example 3 (polymorph D) to a relative humidity of 75% for 3 days.

$^1$H-NMR analysis showed that the crystalline edaravone salt 3-methyl-1-phenyl-2-pyrazolin-5-one hemi-napadisylate monohydrate had been formed.

The crystalline substance was analysed by means of XRPD, DSC and TGA. The results of these analyses are shown in FIGS. 2a (XRPD), 2b (DSC) and 2c (TGA).

The edaravone salt was kept for 28 days at 40° C. and 75% RH without showing significant degradation.

Example 5

A crystalline anhydrous edaravone hemi-napadisylate salt (polymorph E) was prepared by drying the edaravone heminapadisylate monohydrate salt of Example 1 at a temperature of 160° C. for 15 minutes.

¹H-NMR analysis showed that the crystalline edaravone salt was anhydrous 3-methyl-1-phenyl-2-pyrazolin-5-one hemi-napadisylate.

The crystalline substance was analysed by means of XRPD, DSC and TGA. The results of these analyses are shown in FIGS. 5a (XRPD), 5b (DSC) and 5c (TGA).

Example 6

A crystalline anhydrous edaravone heminapadisylate salt (polymorph F) was prepared by solvent equilibration of the edaravone hemi-napadisylate monohydrate salt of Example 1 in methanol/water (97/3). The suspension was thermocycled between room temperature and 50° C. under continuous stirring. During the temperature cycle the salt crystallized. The solid fraction was filtered and dried under vacuum (ambient conditions, 5 mbar). A white crystalline substance was obtained.

¹H-NMR analysis showed that the crystalline edaravone salt was anhydrous 3-methyl-1-phenyl-2-pyrazolin-5-one napadisylate.

The crystalline substance was analysed by means of XRPD, DSC and TGA. The results of these analyses are shown in FIGS. 5a (XRPD), 5b (DSC) and 5c (TGA).

The edaravone salt was kept for 2 days at 40° C. and 75% RH without showing significant degradation.

The invention claimed is:

1. A salt of 3-methyl-1-phenyl-2-pyrazolin-5-one (edaravone), wherein the salt is 3-methyl-1-phenyl-2-pyrazolin-5-one hemi-napadisylate or 3-methyl-1-phenyl-2-pyrazolin-5-one napadisylate.

2. The salt according to claim 1, represented by the following formula:

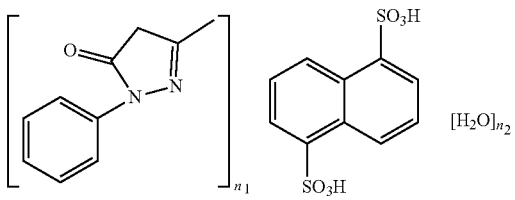

wherein n1 is 1 or 2 and wherein n2 is 0, ½, 1, 2 or 4.

3. The salt according to claim 2, wherein n1 is 2.

4. The salt according to claim 3, wherein n2 is 0, 1 or 2.

5. The salt according to claim 1, wherein the salt is crystalline.

6. The salt according to claim 5, wherein the crystalline salt is a polymorph of edaravone hemi-napadisylate monohydrate salt characterized by an X-ray powder diffraction pattern comprising at least 8 peaks at diffraction angle 2-theta degrees that are within 0.1 degrees of 10.1, 11.3, 11.6, 17.3, 19.6, 20.4, 20.9, 21.1, 21.8, 22.7, 24.6, 26.5 and 27.0 degrees.

7. The salt according to claim 5, wherein the crystalline salt is a polymorph of edaravone hemi-napadisylate monohydrate salt characterized by an X-ray powder diffraction pattern comprising at least 8 peaks at diffraction angle 2-theta degrees that are within 0.1 degrees of 13.1, 14.5, 16.7, 19.5, 21.1, 21.8, 23.3, 23.6, 24.0, 25.6, 26.3 and 30.1 degrees.

8. The salt according to claim 5, wherein the crystalline salt is a polymorph of edaravone hemi-napadisylate monohydrate salt characterized by the single crystal structure shown in the following tables:

| Temperature | 296(2) K |
|---|---|
| λ [Å] | 0.71073 |
| Crystal system | Orthorhombic |
| Space group | P2₁2₁2₁ |
| Unit cell dimensions | |
| a [Å] | 7.9705(6) |
| b [Å] | 18.8542(12) |
| c [Å] | 20.7017(12) |
| V [Å³] | 3111.0(4) |
| Z | 8 |
| $D_c$ [gm/cm³] | 1.436 |
| μ | 0.236 |
| F(000) | 1408 |
| Crystal size [mm³] | 0.25 × 0.18 × 0.15 |
| θ range for data collection [°] | 2.2 → 32.5 |
| Reflections collected | 23655 |
| Independent reflections | 10907 [$R_{int}$ = 0.0600] |
| Completeness to θ = 25.242° [%] | 98.9 |
| Absorption correction | Integration |
| Max. and min. transmission | 0.985 and 0.958 |
| Data/restraints/parameters | 10907/0/521 |
| Goodness-of-fit on$F^2$ | 1.029 |
| Final R indices [I > 2σ(I)] | R1 = 0.0649, wR2 = 0.1115 |
| R indices (all data) | R1 = 0.1278, wR2 = 0.1397 |
| Absolute structure parameter | 0.01(5) |
| Extinction coefficient | n/a |
| Largest diff. peak and hole [e/Å³] | 0.260 and −0.399 |

| | x | y | z | $U_{eq}$ or $U_{iso}$ |
|---|---|---|---|---|
| N1 | 0.9163(5) | 0.6370(2) | 0.74158(17) | 0.0442(8) |
| N2 | 0.8932(5) | 0.6686(2) | 0.68250(19) | 0.0432(9) |
| H2A | 0.852(7) | 0.648(3) | 0.647(3) | 0.067(17) |
| C3 | 0.9546(6) | 0.7346(2) | 0.6845(2) | 0.0419(10) |
| C4 | 0.9459(8) | 0.7816(3) | 0.6276(3) | 0.0650(16) |
| H4A | 1.0007 | 0.8257 | 0.6371 | 0.098 |
| H4B | 0.8306 | 0.7904 | 0.6168 | 0.098 |
| H4C | 1.0008 | 0.7592 | 0.5917 | 0.098 |
| C5 | 1.0188(7) | 0.7467(3) | 0.7454(2) | 0.0454(11) |
| H5A | 1.075(6) | 0.786(3) | 0.761(2) | 0.041(13) |
| C6 | 0.9938(6) | 0.6847(3) | 0.7803(2) | 0.0446(11) |
| O7 | 1.0330(5) | 0.6681(2) | 0.83991(17) | 0.0605(10) |
| H7 | 1.079(10) | 0.705(4) | 0.861(4) | 0.11(3) |
| C8 | 0.8602(6) | 0.5660(3) | 0.7531(2) | 0.0449(11) |
| C9 | 0.8110(7) | 0.5462(3) | 0.8152(3) | 0.0568(13) |
| H9A | 0.819(7) | 0.580(3) | 0.851(2) | 0.058(16) |
| C10 | 0.7521(8) | 0.4783(4) | 0.8250(4) | 0.0710(18) |
| H10A | 0.722(7) | 0.462(3) | 0.866(3) | 0.068(18) |
| C11 | 0.7408(9) | 0.4308(4) | 0.7742(4) | 0.080(2) |
| H11 | 0.699(8) | 0.383(4) | 0.780(3) | 0.10(2) |
| C12 | 0.7913(9) | 0.4513(3) | 0.7130(4) | 0.0754(19) |
| H12A | 0.783(7) | 0.419(3) | 0.676(3) | 0.073(18) |
| C13 | 0.8524(8) | 0.5183(3) | 0.7020(3) | 0.0595(14) |
| H13A | 0.900(7) | 0.534(3) | 0.658(3) | 0.064(16) |
| N21 | 0.9245(5) | 0.8610(2) | 0.23104(17) | 0.0439(8) |
| N22 | 1.0038(5) | 0.8387(2) | 0.17523(19) | 0.0437(9) |
| H22A | 0.995(7) | 0.866(3) | 0.142(2) | 0.060(15) |
| C23 | 1.0624(6) | 0.7729(2) | 0.1833(2) | 0.0432(10) |
| C24 | 1.1514(8) | 0.7352(3) | 0.1309(2) | 0.0594(14) |
| H24A | 1.2641 | 0.7249 | 0.1444 | 0.089 |
| H24B | 1.1541 | 0.7645 | 0.093 | 0.089 |
| H24C | 1.094 | 0.6917 | 0.1213 | 0.089 |
| C25 | 1.0247(7) | 0.7519(3) | 0.2453(2) | 0.0457(12) |
| H25A | 1.048(6) | 0.712(3) | 0.265(2) | 0.042(14) |
| C26 | 0.9363(6) | 0.8071(3) | 0.2736(2) | 0.0433(11) |
| O27 | 0.8663(5) | 0.8136(2) | 0.33083(17) | 0.0586(10) |
| H27 | 0.894(8) | 0.770(3) | 0.353(3) | 0.08(2) |
| C28 | 0.8587(6) | 0.9315(3) | 0.2373(2) | 0.0451(11) |
| C29 | 0.8617(9) | 0.9644(3) | 0.2968(3) | 0.0658(16) |
| H29A | 0.914(7) | 0.939(3) | 0.331(3) | 0.065(17) |
| C30 | 0.7987(10) | 1.0316(4) | 0.3024(4) | 0.082(2) |
| H30A | 0.804(7) | 1.056(3) | 0.344(3) | 0.072(18) |
| C31 | 0.7370(9) | 1.0671(3) | 0.2495(4) | 0.0748(19) |

-continued

| | x | y | z | $U_{eq}$ or $U_{iso}$ |
|---|---|---|---|---|
| H31A | 0.693(8) | 1.114(4) | 0.255(3) | 0.09(2) |
| C32 | 0.7353(8) | 1.0339(3) | 0.1907(4) | 0.0700(17) |
| H32A | 0.703(7) | 1.060(3) | 0.155(2) | 0.059(16) |
| C33 | 0.7942(7) | 0.9658(3) | 0.1839(3) | 0.0573(14) |
| H33A | 0.800(7) | 0.945(3) | 0.145(3) | 0.066(17) |
| O41 | 0.7431(4) | 0.61231(18) | 0.57835(16) | 0.0543(9) |
| O42 | 0.7545(4) | 0.61813(17) | 0.46222(15) | 0.0475(8) |
| O43 | 0.6270(4) | 0.71375(15) | 0.52219(17) | 0.0476(8) |
| S44 | 0.66194(12) | 0.63813(6) | 0.51998(5) | 0.0353(2) |
| C45 | 0.4654(5) | 0.5937(2) | 0.5158(2) | 0.0327(8) |
| C46 | 0.3217(5) | 0.6334(2) | 0.5199(2) | 0.0382(9) |
| H46A | 0.330(6) | 0.682(3) | 0.523(2) | 0.053(14) |
| C47 | 0.1645(6) | 0.6003(2) | 0.5190(2) | 0.0430(10) |
| H47A | 0.067(7) | 0.626(3) | 0.521(3) | 0.068(16) |
| C48 | 0.1511(5) | 0.5291(2) | 0.5141(2) | 0.0404(10) |
| H48A | 0.043(6) | 0.506(2) | 0.516(2) | 0.057(15) |
| C49 | 0.2955(4) | 0.4851(2) | 0.50838(19) | 0.0314(8) |
| C50 | 0.2887(4) | 0.41004(19) | 0.5009(2) | 0.0312(8) |
| S51 | 0.09276(11) | 0.36448(5) | 0.49844(5) | 0.0345(2) |
| O52 | −0.0024(4) | 0.39577(16) | 0.44499(15) | 0.0434(7) |
| O53 | 0.0127(4) | 0.37656(17) | 0.56033(15) | 0.0460(8) |
| O54 | 0.1311(4) | 0.28988(15) | 0.48749(16) | 0.0457(8) |
| C55 | 0.4323(4) | 0.3701(2) | 0.4957(2) | 0.0350(8) |
| H55A | 0.428(6) | 0.317(3) | 0.489(2) | 0.061(15) |
| C56 | 0.5909(5) | 0.4028(2) | 0.4979(2) | 0.0406(10) |
| H56A | 0.691(5) | 0.375(2) | 0.497(2) | 0.047(12) |
| C57 | 0.6026(5) | 0.4744(2) | 0.5054(2) | 0.0382(9) |
| H57A | 0.710(5) | 0.4964(19) | 0.5067(19) | 0.032(11) |
| C58 | 0.4587(4) | 0.51806(19) | 0.5099(2) | 0.0310(8) |
| O61 | 0.9588(6) | 0.7049(2) | 0.39202(19) | 0.0596(11) |
| H61A | 0.900(7) | 0.681(3) | 0.407(3) | 0.049(17) |
| H61B | 1.027(16) | 0.728(5) | 0.430(5) | 0.20(5) |
| O62 | 1.1882(5) | 0.7718(2) | 0.88851(19) | 0.0502(9) |
| H62A | 1.125(9) | 0.803(3) | 0.903(3) | 0.08(2) |
| H62B | 1.252(10) | 0.758(3) | 0.914(3) | 0.09(3) |

9. The salt according to claim 5, wherein the crystalline salt is a polymorph of edaravone hemi-napadisylate hemi-hydrate salt characterized by an X-ray powder diffraction pattern comprising at least 8 peaks at diffraction angle 2-theta degrees that are within 0.1 degrees of 8.4, 11.6, 13.0, 13.6, 13.8, 17.1, 18.8, 19.1, 20.8, 22.6, 24.0, 24.4 and 26.1 degrees.

10. The salt according to claim 5, wherein the crystalline salt is a polymorph of anhydrous edaravone hemi-napadisylate salt characterized by an X-ray powder diffraction pattern comprising at least 7 peaks at diffraction angle 2-theta degrees that are within 0.1 degrees of 10.2, 10.7, 11.1, 12.6, 16.2, 19.1, 19.4, 20.2, 21.7, 22.3 and 26.5 degrees.

11. The salt according to claim 5, wherein the crystalline salt is a polymorph of anhydrous edaravone hemi-napadisylate salt characterized by an X-ray powder diffraction pattern comprising at least 7 peaks at diffraction angle 2-theta degrees that are within 0.1 degrees of 11.54, 13.91, 14.09, 16.84, 18.25, 18.55, 19.11, 22.39, 22.76, 24.63 and 25.58 degrees.

12. A pharmaceutical composition comprising 3-methyl-1-phenyl-2-pyrazolin-5-one hemi-napadisylate or 3-methyl-1-phenyl-2-pyrazolin-5-one napadisylate.

13. The pharmaceutical composition according to claim 12, wherein the composition is an oral dosage unit, a powder, an aqueous liquid or a transdermal delivery system.

14. A method of treating a mammal suffering from amyotrophic lateral sclerosis (ALS) or stroke, comprising administering to the mammal a pharmaceutical composition comprising 3-methyl-1-phenyl-2-pyrazolin-5-one hemi-napadisylate or 3-methyl-1-phenyl-2-pyrazolin-5-one napadisylate.

15. A method of preparing 3-methyl-1-phenyl-2-pyrazolin-5-one napadisylate or 3-methyl-1-phenyl-2-pyrazolin-5-one hemi-napadisylate, the method comprising:

(a) providing an edaravone solution containing 3-methyl-1-phenyl-2-pyrazolin-5-one in cationic form;

(b) combining the edaravone solution with napadisylate or napadisylate solute; and (c) precipitating 3-methyl-1-phenyl-2-pyrazolin-5-one napadisylate and/or 3-methyl-1-phenyl-2-pyrazolin-5-one hemi-napadisylate.

\* \* \* \* \*